United States Patent [19]
Rebek, Jr. et al.

[11] Patent Number: 5,877,030
[45] Date of Patent: Mar. 2, 1999

[54] PROCESS FOR CREATING MOLECULAR DIVERSITY AND NOVEL PROTEASE INHIBITORS PRODUCED THEREBY

[76] Inventors: Julius Rebek, Jr., 100 Memorial Dr., #5-3A, Cambridge, Mass. 02142; Thomas Carell, 43 Porter Rd., Cambridge, Mass. 02140; Edward A. Wintner, 550 Memorial Dr., #19B1, Cambridge, Mass. 02139

[21] Appl. No.: 454,861

[22] Filed: May 31, 1995

Related U.S. Application Data

[63] Continuation of Ser. No. 282,083, Jul. 28, 1994, abandoned, which is a continuation-in-part of Ser. No. 180,215, Jan. 12, 1994, abandoned.

[51] Int. Cl.$^6$ ....................... G01N 33/543; C07D 311/82
[52] U.S. Cl. ......................... 436/518; 436/528; 549/388; 549/392
[58] Field of Search ............................. 435/7.1; 436/501, 436/518, 528; 549/388, 392

[56] References Cited

U.S. PATENT DOCUMENTS

| | | | |
|---|---|---|---|
| 4,833,332 | 5/1989 | Robertson, Jr. et al. | 250/458.1 |
| 4,963,654 | 10/1990 | Katanuma | 530/324 |
| 5,010,175 | 4/1991 | Rutter et al. | 530/334 |
| 5,071,988 | 12/1991 | Failli et al. | 546/174 |
| 5,109,018 | 4/1992 | Powers et al. | 514/457 |
| 5,157,019 | 10/1992 | Glover et al. | 514/12 |
| 5,192,668 | 3/1993 | Treiber et al. | 435/41 |
| 5,240,913 | 8/1993 | Maraganore et al. | 514/13 |
| 5,250,677 | 10/1993 | Han | 540/200 |

FOREIGN PATENT DOCUMENTS

| | | |
|---|---|---|
| WO-A- 8607061 | 12/1986 | WIPO . |
| 91/18598 | 12/1991 | WIPO . |
| WO93/09668 | 5/1993 | WIPO . |

OTHER PUBLICATIONS

Shinaki et al: Chem. Abs. vol. 117, abstract No. 198267t, 1992.
Novel Approaches to Small Molecular Library Screening, T. Carell et al., Conference Exploiting Molecular Diversity, Jan. 12–14, 1994, San Diego, Combinational Libraries for Drug Discovery.
Nonpeptidal Peptidomimetics with a β–D–Glucose Scaffolding. A Partial Somatostatin Agonist Bearing a Close Structural Relationship to a Potent, Selective Substance P Antagonist, R. Hirschmann et al., J. Am Chem Soc., 1992, 114, 9217–9218.
The First Design and Synthesis of a Sterioidal Peptidomimetic. The Potential Value of Peptidomimetics in Elucidating the Bioactive Conformation of Peptide Ligands, R. Hirschmann et al., J. Am Chem Soc., 1992, 114, 9699–9701.
Design, Synthesis, and Crystal Structure of a Pyrrolinone–Based Peptidomimetic Possessing the Conformation of a β–Strand: Potential Application to the Design of Novel Inhibitors of Proteolytic Enzymes, A. Smith III et al., J. Am Chem Soc., 1992, 114, 10672–10674.
Selection of single–stranded DNA molecules that bind and inhibit human thrombin, L. Bock et al., Nature, 355, Feb. 6, 1992, 564–566.
The Generation of Molecular Diversity, M. Pavia et al., Bioorganic & Medicinal Chemistry Letters, vol. 3, No. 3, pp. 387–396, 1993.
Multiple Peptide Synthesis Methods and Their Aplications, G. Jung et al., Angew. Chem. Int. Ed. Engl. 31 (1992) 367–383.
Strategies for epitope analysis using peptide synthesis, H. Geysen et al., Journal of Immunological Methods, 102 (1987) 259–274.
The Simultaneous Multiple Production of Solution Phase Peptides; Assessment of the Geysen Method of Simultaneous Peptide Synthesis, A. Bray et al., Tetrahedron Letters, vol. 31, No. 40, pp. 5811–5814, 1990.
Light–Directed, Spatially Addressable Parallel Chemical Synthesis, S. Fodor et al., Science, vol. 251, Feb. 15, 1991 pp. 767–773.
Simultaneous Multiple Peptide Synthesis: The Rapid Preparation of Large Numbers of Discrete Peptides for Biological, Immunological, and Methodological Studies, R. Houghten et al., BioTechniques, vol. 4, No. 6 (1986) 522–528.
General method for rapid synthesis of multicomponent peptide mixtures, A. Furka et al., Int. J. Peptide Protein Res. 37, 1991, 487–493.
Generation and use of synthetic peptide combinatorial libraries for basic research and drug discovery, R. Houghten et al., Nature, vol. 354, Nov. 7, 1991, pp. 84–86.
A new type of synthetic peptide library for identifying ligand–binding activity, K. Lam et al., Nature, vol. 354, Nov. 7, 1991, pp. 82–84.
Searching for Peptide Ligands with an Epitope Library, J. Scott et al., Science, vol. 249, Jul. 27, 1990, pp. 386–390.
Random Peptide Libraries: A Source of Specific Protein Binding Molecules, J. Devlin et al., Science, vol. 249, Jul. 27, 1990, pp. 404–406.
Peptides on phage: A vast library of peptides for identifying ligands, S. Cwirla et al., Proc. Natl. Acad. Sci. USA, vol. 87, pp. 6378–6382, Aug. 1990.
Peptoids: A modular approach to drug discovery, R. Simon et al., Proc. Natl. Acad. Sci. USA, vol. 89, pp. 9367–9371, Oct. 1992.
Semisynthetic combinatorial antibody librarxes: A chemical solution to the diversity problem, C. Barbas, III et al., Proc. Natl. Acad. Sci. USA, vol. 89, pp. 4457–4461, May 1992.
Encoded combinatorial chemistry, S. Brenner et al., Proc. Natl. Acad. Sci. USA, vol. 89, pp. 5381–5383, Jun. 1992.

(List continued on next page.)

*Primary Examiner*—Ponnathapura Achutamurthy

[57] ABSTRACT

Methods for forming combinatorial libraries and the libraries produced thereby are provided. According to a preferred aspect of the invention, a plurality of core molecules are reacted with a plurality of different tool molecules to form a library of molecules having non-naturally occurring molecular diversity. The libraries are useful for identifying lead compounds which modulate the functional activity of a biological molecule. Protease inhibitors that have been isolated from the libraries also are disclosed.

18 Claims, 16 Drawing Sheets

OTHER PUBLICATIONS

Peptide ligands for a sugar–binding protein isolated from a random peptide library, K. Oldenburg et al., Proc. Natl. Acad. Sci. USA, vol. 89, pp. 5393–5397, Jun. 1992.

Identification of highest–affinity ligands by affinity selection from equimolar peptide mixtures generated by robotic synthesis, R. Zuckermann et al., Proc. Natl. Acad. Sci. USA, vol. 89, pp. 4505–4509, May 1992.

Synthetic Compounds Mimic Peptide β–Pleated Sheet Motif, S. Borman, C&EN, Feb. 8, 1993, pp. 27–28.

Alex, Brown & Sons, Inc., Research Life Sciences/Biotechnology Group, Apr. 28, 1992.

First Boston, Equity Research, Industry: Biotechnology, Mar. 6, 1992.

Goldman, Sachs & Co., Investment Research report on Affymax N.V.

Companies . . . companies news brief, Scrip No. 1752, Sep. 11, 1992, pp. 12–13.

Sigma Chemical Co. Catalog, 1991, "Tissue Culture Media and Reagents", pp. 850 and 1549.

Digestion 1994;55(2):90–6, "Monitoring Serum Tryptic Activity and Effect of Trypsin Inhibitor on Rat Acute Pancreatitis", H. Sobajima et al.

Arnold–Stanton, R. and D. Lemal, Tandem Nucleophilic Additions of Aryloxides, J. Org. Chem, vol. 56, No. 1, 1991, 151–157.

Leytus, S., New class of sensitive and selective fluorogenic substrates for serine proteinases, Biochem J. (1983) 215, 253–260.

Morgan et al., Annual Reports in Medicinal Chemistry, Vo. 24 pp. 243–252 (1989) "Approaches to the Discovery of Non–Peptide Ligands for Peptide Receptors and Peptidases".

X = reactive center
Planar aromatic or heterocycle, e.g.:

Examples of amino acids and other amines suitable for use as tools in the generation of diversity
X = H, Me, Et, t-Bu
Y = H or protetcting group Examples of nucleobases and modified nucleobases suitable for use as tools in the generation of diversity.

X = functional group to react with reactive center on core molecule
Y = H or protecting group Core molecule      Tools with functionality X Core molecule      Tools with functionality X Core molecule      Tools with functionality X Core molecule     Tools with functionality X Core molecule     Tools with functionality X Core molecule     Tools with functionality X Core molecule    Tools with functionality X Core molecule    Tools with functionality X Synthesis and HPLC analysis of a library of 136 theoretical items.

X = Mixture of:

Ala-OMe        Trp-OMe
Phe-OMe        Val-OMe

Synthesis and HPLC analysis of a library of 1225 theoretical items.

X = Mixture of:

| | |
|---|---|
| Ala-OMe | Trp-OMe |
| Leu-OMe | Met-OMe |
| Pro-OMe | Val-OMe |
| Phe-OMe | |

Synthesis and HPLC analysis of a library of 10,440 theoretical items.

X = Mixture of:

| | |
|---|---|
| Ala-OMe | Phe-OMe |
| Leu-OMe | Met-OMe |
| Pro-OMe | Asp(OtBut)-OMe |
| Lys(Boc)-OMe | Val-OMe |
| Ser(tBut)-OMe | Glu(OtBut)-OMe |
| His(Trt)-NH-$C_3H_7$ | Furfurylamine derivative |

Synthesis and HPLC analysis of a library of 97,461 theoretical items.

X = Mixture of:

Ala-OMe
Asp(OtBu)-OMe
Glu(OtBu)-OMe
Ile-OtBu
Leu-OMe
Met-OMe
Phe-OMe
Pro-OMe
Ser(tBu)-OMe
Thr(tBu)-OMe
Lys(Boc)-OMe

Trp-OMe
Tyr(tBu)-OMe
Val-OMe

Arg(Mtr)-NH-CH$_2$C$_6$H$_4$OMe
Cys(Trt)-NH-CH$_2$C$_6$H$_5$
Val-NH-Cyclohexane
His(Trt)-NH-C$_3$H$_7$
Furfurylamin derivative
Pyrrole derivative
CH$_2$C$_6$H$_4$OMe Tetra-acid chloride Di-acid chloride 1                              2

V

VI

PROCESS FOR CREATING MOLECULAR DIVERSITY AND NOVEL PROTEASE INHIBITORS PRODUCED THEREBY

RELATED APPLICATIONS

This application is a continuation of application Ser. No. 08/282,083 filed Jul. 28, 1994, now abandoned, which is a continuation-in-part of application Ser. No. 08/180,215, filed Jan. 12, 1994, now abandoned, the entire contents of which are incorporated herewith.

GOVERNMENT SUPPORT

The invention described herein was supported in part by grant number GM 27932 from the National Institute of Health.

FIELD OF THE INVENTION

This invention relates to methods for generating combinatorial libraries and to the libraries produced thereby. The libraries are useful for identifying pharmaceutical and agricultural lead compounds. This invention also relates to novel biologically active enzyme inhibitors. More particularly, the invention relates to novel molecules which bind to and inhibit serine proteases, including, for example, trypsin.

BACKGROUND OF THE INVENTION

A need exists to identify novel lead compounds that are capable of modulating pharmaceutical and agricultural molecular reactions. Historically, such novel compounds were identified by individually synthesizing a compound and testing it for biological activity. This time-consuming process has been replaced, in part, by a process referred to as "rational drug design". This traditional route to drug discovery requires a knowledge of the structure of the target (i.e., ligate) and/or its cognate (i.e., ligand) in order to synthesize only those molecules which are structurally-related to known ligands of the biological target. However, despite this more focussed approach to identifying lead compounds, the time requirements for conventional structural analysis and chemical synthesis of complex molecules continues to contribute to the substantial periods of time consumed by research and development in the discovery of novel drugs.

The application of recombinant technology and automated methods for solid phase chemical synthesis to the generation of molecularly diverse libraries has circumvented many of the most time-consuming steps associated with the traditional drug discovery process. As a result of these technological advances, "rational drug design" rapidly is being replaced by "irrational drug design", i.e., the process of screening libraries of molecularly diverse molecules to identify biologically active molecules contained therein (Brenner, S., and Lerner, R., *Proc. Natl. Acad. Sci. USA* 89:5381–5383 (1992)).

Recombinant molecular libraries are generated by inserting random segments of nucleic acid into a vector, such as a phage, and allowing the vector to replicate, transcribe and express the inserted sequence. In a phage library, the nucleic acid is inserted into the phage genome in a manner which permits expression of the inserted material on the phage surface (see, e.g., Pavia, M., et al., *Bioorg. & Med. Chem. Ltrs.* 3(3):387–396 (1993) and references cited therein; Devlin, J., et al., *Science* 249:404–406 (1990)). Typically, the virus particles are screened for the presence of a lead compound by contacting the particles with an immobilized ligate and isolating the virus particles which express a ligand that binds to the immobilized ligate.

The primary advantage of using a recombinantly-produced library for drug discovery is the ability to clone and amplify the nucleic acids encoding the lead compounds which are identified during the screening process. Unfortunately, recombinant libraries inherently are limited in diversity to linear polymers (e.g., oligonucleotides, peptides) formed of naturally-occurring monomers (e.g., nucleotides, L-amino acids). Typically, these naturally-occurring polymers exhibit metabolic instability and poor absorption properties in vivo. Accordingly, pharmaceutical lead compounds that are isolated from recombinant libraries frequently require substantial modification to obtain a clinically useful drug.

To overcome these limitations, a number of chemical methods have been used to generate molecular libraries. In general, such methods utilize a solid support (e.g., cellulose paper, cotton, polystyrene-grafted polyethylene film, polymeric beads and resins) upon which a diverse collection of linear compounds are synthesized using conventional coupling chemistries (e.g., Merrifield, *J. Am. Chem. Soc.* (1963) 85:2149–2154). The synthesis of libraries containing molecularly diverse peptides has become commonplace since Geysen et al. first reported the chemical synthesis of a peptide library on polyacrylic acid grafted polyethylene pins (Geysen, H., et al., *J. Immunolog. Meth.* 102:259–274 (1987)). More recently, Houghten et al. (*BioTechniques* 4(6):522–528 (1986) and *Nature* 354:84–86 (1991)) described a method for generating peptide libraries in which small amounts of a resin support were encapsulated in a plurality of porous polypropylene bags. By sequentially immersing the bags in solutions of individual amino acids under conditions for forming a peptide linkage, Houghten et al. generated a collection of bags, each of which contained a unique resin-immobilized peptide. The generation of combinatorial bead-immobilized peptide libraries also has been reported using a split synthesis procedure (Lam, K., et al., *Nature* 354:82–84 (1991). Solid-phase peptide synthesis also has been combined with photolithography to prepare arrays of peptides or oligonucleotides attached to solid supports (Fodor, S., et al., *Science* 251:767–773 (1991)).

Although chemically-synthesized libraries offer nearly unlimited molecular diversity, it typically is necessary that small library molecules be cleaved from the solid support prior to assessing biological activity. Moreover, the above-recited methods typically produce libraries of linear polymers in which monomers are connected via a biological backbone (e.g., a polypeptide backbone of amide linkages connecting amino acid monomers). Because such structures are recognized by degradative enzymes in vivo, many chemically-synthesized library molecules also are metabolically unstable.

Frequent attempts have been made to identify compounds which inhibit the enzymatic activity of proteases and in particular, to identify inhibitors of serine proteases. The serine proteases are a family of enzymes that utilize an activated serine residue in their substrate binding domain to hydrolyze peptide bonds. See, e.g., "Textbook of Biochemistry", 3rd edition, ed. T. Devlin, N.Y., N.Y., John Wiley & Sons, Inc., pp.102–116 (1992). The Devlin textbook, as well as each of the references, patent publications and patents identified in this application, are incorporated in their entirety herein by reference.

Abnormally high levels of serine proteases have been implicated in the following physiological conditions (the serine protease believed to mediate the condition appears in parentheses): pancreatitis (trypsin, chymotrypsin, pancreatic elastase, enterokinase); cerebral infarction, coronary infarction, thrombosis, bleeding disorders (plasma kallikrein, Factors XIIa, XIa, IXa, VIIa, Xa and IIa (thrombin) and Activated Protein C); inflammation, rheumatoid arthritis, autoimmune disease (Factors C1r, C1s, D, B and C3 Convertase); clotting disorders, tumor metastasis (urokinase plasminogen activator, tissue plasminogen activator, plasmin); infertility (acrosin); and inflammation, allergic response (granulocyte elastase, Cathepsin G, mast cell chymases, mast cell tryptases). Accordingly, agents which reduce or eliminate the catalytic activity of these enzymes, i.e., serine protease inhibitors, are useful for treating individuals diagnosed as having the above-mentioned serine protease-mediated physiological conditions.

Several naturally-occurring serine protease inhibitors have been identified and isolated. These inhibitors are believed to play a key role in the regulation of serine protease activity in vivo. In view of the clinical significance of the serine protease inhibitors, early efforts to identify serine protease inhibitors focussed on isolating peptide inhibitors from mammalian tissue, chemically synthesizing inhibitors having the same amino acid sequence as the natural peptide inhibitors and/or chemically (or otherwise) modifying the natural (or chemically equivalent) peptide inhibitors.

U.S. Pat. No. 4,963,654, issued to Katunuma, describes a naturally-occurring trypsin inhibitor that is isolated from animal tissue. The inhibitor is a basic peptide containing L-amino acids and has a molecular weight of about 7,600. U.S. Pat. No. 5,157,019, issued to Glover et al. also describes novel peptides which exhibit inhibitory activity toward serine proteases. The Glover et al. inhibitory peptides include a generic inhibitory amino acid core sequence that is recognized by several different proteases. The inhibitory core sequence contains between about eleven and about thirty-one amino acid residues. U.S. Pat. No. 5,240,913, issued to Marganore et al. describes a thrombin inhibitor which contains naturally-occurring, as well as non-naturally occurring amino acids.

Chemically synthesized serine protease inhibitors are disclosed in U.S. Pat. No. 5,250,677, issued to Han (hereinafter "Han '677") and U.S. Pat. No. 5,109,018, issued to Powers et al. (hereinafter "Powers et al. '018"). Han '677 describes the synthesis of azetidin-2-one derivatives and their use as serine protease inhibitors. In particular, Han '677 report that the derivatives exhibit anti-thrombin and anti-trypsin activities and are useful in controlling blood coagulation and treating pancreatitis.

Powers et al. '018 describes the synthesis of heterocyclic compounds and reports that these compounds inhibit serine proteases having chymotrypsin-like, elastase-like and trypsin-like specificities. Powers et al. further report that these compounds are useful for treating physiological conditions which involve tissue proteolysis (e.g., emphysema), as well as for preventing undesired proteolysis that occurs during the production, isolation, purification, transport and storage of valuable peptides and proteins.

A biotransformed heterocyclic compound, described in U.S. Pat. No. 5,192,668, issued to Treiber et al., reportedly exhibits inhibitory activity toward a protease present in the HIV virus. The biotransformed molecule is prepared by culturing a particular Streptomyces culture in the presence of a known HIV protease inhibitor to yield a biotransformed molecule having anti-HIV protease inhibitor activity.

Despite the developments in genetic engineering, rational drug design and the recognition of the clinical and industrial value of developing more potent, biologically-stable serine proteases, few serine protease inhibitors having the requisite activity for inhibiting the catalytic activity of proteases in vivo and/or in vitro to accomplish the above-described clinical and industrial objectives have been identified. Accordingly, a need exists to identify, select and manufacture serine proteases inexpensively and in commercially reasonable quantities to achieve these goals.

SUMMARY OF THE INVENTION

The present invention overcomes the limitations of the prior art by providing a simple, solution phase process for generating tens of thousands of molecularly diverse molecules. In the preferred embodiments, the library molecules have structures that are not recognized by degradative enzymes in vivo, a feature which contributes to the metabolic stability and improved absorption properties of these molecules in vivo. By selecting the appropriate core molecules (discussed below) and tool molecules (discussed below) for forming the library, the conformation (e.g., linear, spherical, disc-like) of the library molecules can be preselected.

According to one aspect of the invention, a method for forming a combinatorial library is provided. The method includes (a) admixing a plurality of core molecules having at least one reactive center with a plurality of different tool molecules, each having at least one functional group to form a reaction mixture, and (b) reacting the reactive centers of the core molecules with the functional groups of the tool molecules to form a plurality of library molecules. To identify pharmaceutical and/or agricultural lead compounds, the combinatorial library is screened for the presence of molecules having biological activity, for example, by identifying library molecules which modulate the biological activity of a ligate (i.e., a molecule which is capable of specifically recognizing and associating with a ligand). The core molecule primarily serves as a scaffold to which different tool molecules can be attached at a fixed spatial orientation relative to one another. By combining naturally and/or non-naturally occurring core molecules and tool molecules in accordance with the methods disclosed herein, the instant invention provides a simple, one-step process for creating a combinatorial library of vast molecular diversity. Complementary pairs of reactive centers and functional groups are selected so that the reactive centers are capable of reacting with the functional groups to form the library molecules. In a particularly preferred embodiment, the reactive center is an acid halide, the functional group is an amine and the library molecule is a non-naturally occurring molecule in which the core molecule and the tool molecule(s) are linked via an amide bond. Alternative complementary pairs of reactive centers and functional groups are familiar to those skilled in the art.

According to another aspect of the invention, a method for manufacturing a combinatorial library having molecular diversity is provided. The method includes (a) admixing a plurality of core molecules having at least one reactive center with a plurality of different tool molecules to form a reaction mixture, each tool molecule including a first functional group for reacting with the reactive center and a second functional group attached to a removable, fat-soluble protecting group; (b) reacting the reactive centers of the core molecules with the functional groups of the tool molecules to form a pro-library of fat-soluble molecules; and (c) extracting the unreacted core molecules and the unreacted tool molecules from the pro-library molecules. The tool molecule may contain more than two functional groups (e.g., a third functional group, a fourth functional group), each of which may be attached to a protecting group. optionally, the protecting groups are removed from the pro-library of molecules to form a second combinatorial library.

According to yet another aspect of the invention, an alternative method for manufacturing a combinatorial library is provided. The method includes reacting a plurality of core molecules, each having at least two reactive centers at a fixed spatial orientation relative to one another, with a plurality of different tool molecules, so that the reactive centers of the core molecules react with the functional groups of the tool molecules to form a library of molecules, each containing tool molecules located at a fixed spatial orientation relative to one another.

According to still another aspect of the invention, a fat-soluble combinatorial pro-library is provided. As will be apparent to one of ordinary skill in the art, the terms "fat-soluble" and "water-soluble" express the relative degree of solubility of a compound in an organic ("fat") phase or in an aqueous ("water") phase. Thus, a compound or molecule is said to be "fat-soluble" if it is more soluble in an organic phase than it is in an aqueous phase. The fat-soluble pro-library contains a plurality of non-naturally occurring molecules, each molecule including at least one tool molecule linked to a core molecule. In the preferred embodiments, the tool molecules further include a removable (e.g., cleavable) protecting group, the inclusion of which group in the non-naturally occurring molecule renders the latter molecule fat-soluble. The fat-soluble pro-library is useful for identifying pharmaceutical and/or agricultural lead compounds which modulate the functional activity of, for example, a membrane-associated biological molecule. Removal of the fat-soluble protecting group from the library molecule (e.g., by cleaving the group from the library molecule) and removal of the cleaved protecting group from the reaction mixture (e.g., by extraction) yields a water-soluble library which also can be screened for the presence of pharmaceutical and/or agricultural lead compounds.

According to another aspect of the invention, a library containing a plurality of structurally-diverse non-naturally occurring molecules is provided. The non-naturally occurring molecules include a first tool molecule and a second tool molecule covalently coupled to a core molecule at a fixed spatial orientation. Within a combinatorial library, the first and second tool molecules may be coupled to the core molecule at the same fixed spatial orientation or at a different fixed spatial orientation. Such combinatorial libraries are useful, for example, for determining the optimal spatial orientation of tool molecules relative to one another in a lead compound or group of lead compounds, e.g., by comparing the biological activities of lead compounds identified in combinatorial libraries which differ from one another only in the spatial orientation of the tool molecules or alternatively, by empirically determining the spatial orientation in lead compound(s) identified in a library containing molecules in which the first and second tool molecules are coupled to the core molecule at different fixed spatial orientations.

According to yet another aspect of the invention, a kit for forming a combinatorial library is provided. The kit includes a plurality of core molecules, each having at least one reactive center and instructions for reacting the core molecules with a plurality of tool molecules to form a combinatorial library. Preferably, the kit further includes the plurality of different tool molecules, each having at least one functional group.

According to still another aspect of the invention, a combinatorial library of non-naturally occurring molecules is provided. The library includes a plurality of non-naturally occurring molecules, each including at least one tool molecule covalently coupled to a xanthene molecule. The tool molecules are selected from the group consisting of an amino acid and a nucleoside.

According to yet another aspect of. the invention, an isolated compound of the formula (hereinafter "Formula I"):

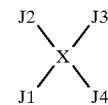

is disclosed. The isolated compound includes a core molecule, "X", to which is covalently attached each of four tool molecules (J1, J2, J3 and J4) at a fixed spatial orientation relative to one another. Preferably, the isolated compound exhibits an anti-enzyme activity, more preferably an anti-serine protease activity. Thus, in a particularly preferred embodiment, the isolated compound is a serine protease inhibitor. As used herein, the terms "inhibitor" and "anti-enzyme" are used interchangeably to refer to a compound which reduces or eliminates the catalytic activity of an enzyme. Thus, an anti-serine protease is a compound which reduces or eliminates the catalytic activity of a serine protease.

Core molecule "X" is xanthene or a "xanthene spatial analog", i.e., a molecule that maintains each tool molecule at approximately the same fixed spatial orientation with respect to one another that would result had the tool molecules been covalently attached to xanthene positions 2, 4, 5 and 7. The preferred inhibitor of the invention includes a xanthene core molecule to which tool molecules J1, J2, J3 and J4 are covalently coupled at xanthene positions 2, 4, 5 and 7, respectively.

In a particularly preferred embodiment, the inhibitor includes a xanthene core molecule to which tool molecules J1, J2, J3 and J4 (L-Valine (Val), L-Lysine-methyl ester (Lys-methyl ester), L-Isoleucine (Ile) and L-Proline (Pro), respectively), are covalently attached at xanthene positions 2, 4, 5 and 7 (hereinafter the compound of "Formula V"). Alternatively, the inhibitor can include a xanthene core molecule to which tool molecules J1 (Pro), J2 (Val), J3 (Ile) and J4 (Lys-methyl ester) are covalently attached at xanthene positions 2, 4, 5 and 7 (hereinafter the compound of "Formula VI"). Throughout this application, the conventional three letter amino acid code has been used to denote L-amino acids unless otherwise indicated. (See, e.g., Devlin, "Textbook of Biochemistry", supra.). That rational modifications or substitutions for the above-identified amino acids and/or amino acid derivatives can be made without substantially changing the anti-trypsin activity of the compounds of Formulas V and VI would be apparent to one of ordinary skill in the art. Such modifications and substitutions are described in more detail below.

According to another aspect of the invention, a pharmaceutical composition for use in treating a physiological condition caused by an elevated level of a serine protease is provided. The pharmaceutical composition includes a pharmaceutically acceptable carrier and a therapeutically effective amount of one or more of the above-described serine protease inhibitors. The pharmaceutical composition is prepared by placing the above-described inhibitor in a pharmaceutically acceptable carrier.

The invention also provides a method of treating a subject (i.e., a mammal, preferably a human) diagnosed as having a physiological condition that is caused by an abnormally elevated level of a serine protease. The method involves administering to the subject a therapeutically effective amount of the above-described pharmaceutical composition to inhibit the in vivo activity of the serine protease. Preferably, the serine protease is trypsin and the preferred trypsin inhibitor (the compound of Formula V) is administered to the subject to reduce the abnormally elevated level of trypsin activity in vivo, thereby alleviating (or preventing) the symptoms manifested by the physiological condition.

According to yet another aspect of the invention, a trypsin inhibitor solution for use in cell culture is provided. The solution includes a cell culture medium and an effective amount of a trypsin inhibitor of the invention to inhibit the enzymatic activity of trypsin in vitro. Following trypsinization to remove adherent cells from a culture surface, the cells are resuspended in the trypsin inhibitor solution to inactivate trypsin remaining in the cell suspension, thereby preventing trypsin-mediated damage to the cells.

According to yet another aspect of the invention, a method of preventing undesired proteolysis of a peptide or protein by a serine protease is provided. The method involves contacting the peptide or protein with an effective amount of a serine protease inhibitor of the invention to inhibit the enzymatic activity of the protease. In a particularly preferred embodiment in which the inhibitor is used to inhibit the in vitro activity of a protease, the above-described trypsin inhibitor (Formula V) is added to preparations containing antibodies, enzymes, plasma proteins, tissue extracts, or other peptides and/or proteins that are used in clinical analysis and/or biomedical research, to prevent the undesired proteolysis of these valuable peptides and/or proteins.

These and other aspects of the invention as well as various advantages and utilities will be more apparent with reference to the detailed description of the preferred embodiments and in the accompanying drawings.

DETAILED DESCRIPTION OF THE INVENTION

I. Glossary of terms

As used herein, the following terms are intended to have the following meanings:

Chemical and Biological Terms: have their common meanings known to one of ordinary skill in the art unless otherwise indicated.

Combinatorial Library: refers to a collection of structurally-diverse molecules. Hence, the libraries of the invention are said to have molecular diversity. As will be explained in more detail below, the extent of this diversity is dictated by the number, the nature and the ratio of the reactants (i.e., the core molecules and tool molecules) which react. to form the library molecules. Although the core molecules and tool molecules may be naturally-occurring or non-naturally occurring, the reaction product of the reaction between the core and tool molecules typically is a non-naturally occurring molecule. Thus, in general, the libraries of the invention are said to have non-naturally occurring molecular diversity.
Library Molecules: refers to the plurality of molecules which comprise a combinatorial library. Library molecules are the products of the reaction between the core molecules and the tool molecules (defined below).
Core Molecule: refers to a molecule having a rigid or relatively rigid molecular structure (discussed below) and including at least one reactive center for reacting with a functional group of a tool molecule (defined below). The core molecule serves as a scaffold to which the tool molecules can be linked in a fixed spatial orientation (defined below) relative to one another.

Examples of core molecules that can be used in accordance with the methods of the invention, include, but are not limited to, chemical compounds (e.g., monocyclic molecules, polycyclic molecules, heterocyclic molecules, aromatic molecules) and biochemical compounds (e.g., adenine, thymine, guanine, cytidine, uracil, inosine, as well as analogs, nucleosides, and nucleotides of the foregoing nucleobases). Thus, core molecules also include pharmaceutical molecules which have a known biological activity and fragments of such pharmaceutical molecules.

Figure 1:
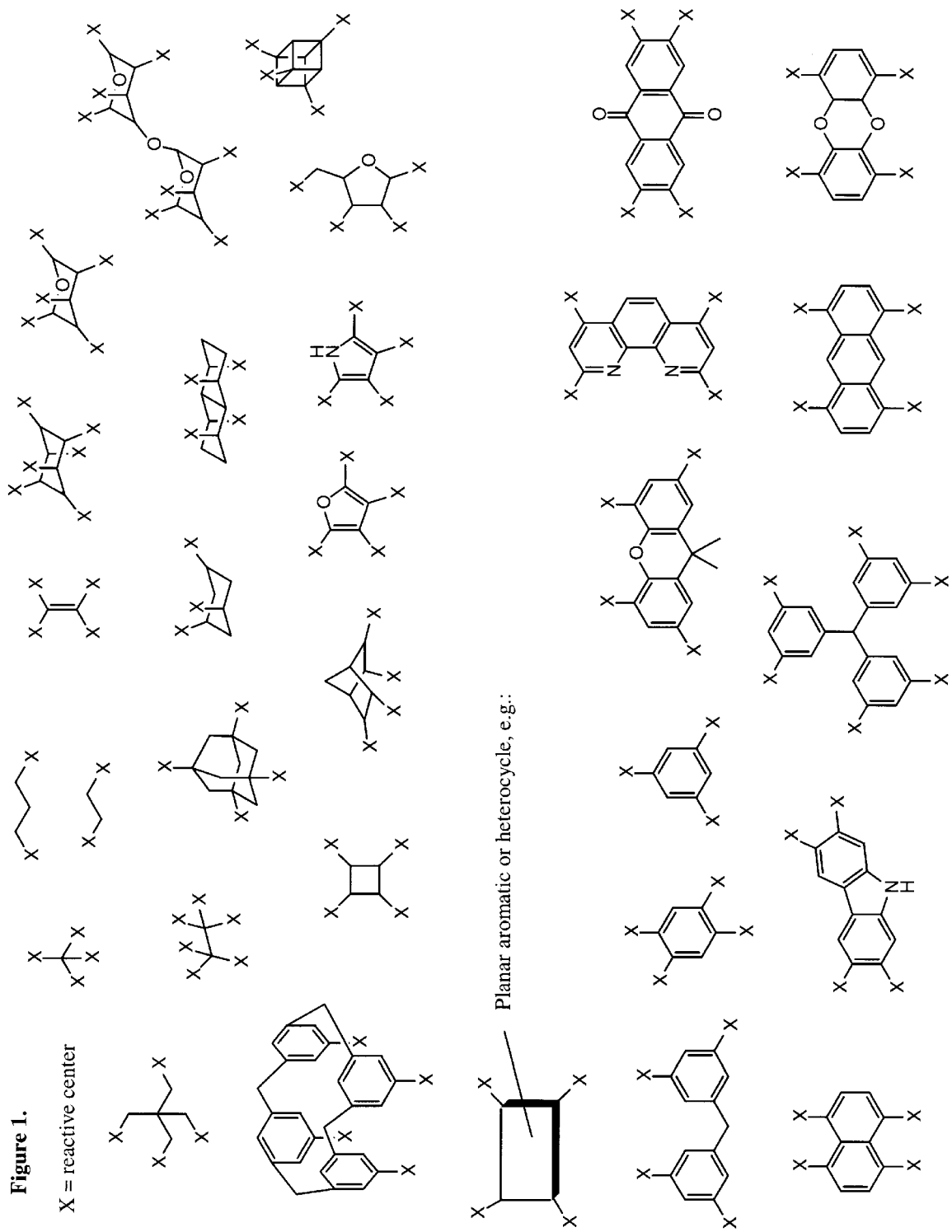
FIG. 1 shows exemplary core molecules for generating the combinatorial libraries of the invention (in which the structures represent carbon cores except were noted)

Examples of the foregoing categories of chemical compounds are provided in FIG. 1. In general, the planar aromatic and planar heterocyclic molecules shown in FIG. 1 exemplify a class of rigid core molecules and the non-aromatic monocyclic and polycyclic molecules shown in the figure exemplify a class of relatively rigid molecules. In a particularly preferred embodiment, the core molecule is selected from the group consisting of 9,9-dimethylxanthene-2,4,5,7-tetraacid chloride and 1,3,5,7-cubane tetraacid chloride (see, e.g., A. Bashir-Hashemi, *Angew. Chem.* (Intl. Ed. in English) 32:612–613 (1993) for a synthesis procedure for the cubane tetraacid chloride). In the preferred embodiments, the core molecule includes two or more reactive centers (described below) for forming a covalent linkage with the functional groups of the tool molecules. Thus, following formation of the covalent linkage, the core molecules have a sufficiently rigid structure to maintain two or more tool molecules at a fixed spatial orientation relative to one another.

Reactive Center: refers to a reactive group of the core molecule which is capable of forming a linkage (e.g., a covalent bond) with a complementary functional group (described below) of the tool molecule. For a linkage-forming reaction which follows a nucleophilic/electrophilic mechanism (discussed below), the reactive center can be a nucleophile (e.g., an alcohol, an amine, a thiol) or an electrophile (e.g., an acid halide, an alkyl halide). In a particularly preferred embodiment, the reactive center is an acid chloride and the functional group of the tool molecule is an amine, an alcohol or a thiol group. Alternative types of reaction mechanisms can be used to form the linkage between the core molecule and the tool molecule(s). For example, palladium can be used to catalyze the reaction between the reactive centers of the core molecules and the functional groups of the tool molecules to form the combinatorial library molecules. (See, e.g., N. Miyaura, H. Suginome, and A. Suzuki, *Tetrahedron Ltrs.* 22:127–130 (1981)). Other mechanisms for forming a covalent linkage between the core molecules and tool molecules of the invention are known to those of ordinary skill in the art. (See, e.g., March, J., *Advanced Organic Chemistry*, 4th Ed., New York, N.Y., Wiley and Sons, 1985), pp.326–1120).

Figure 2:
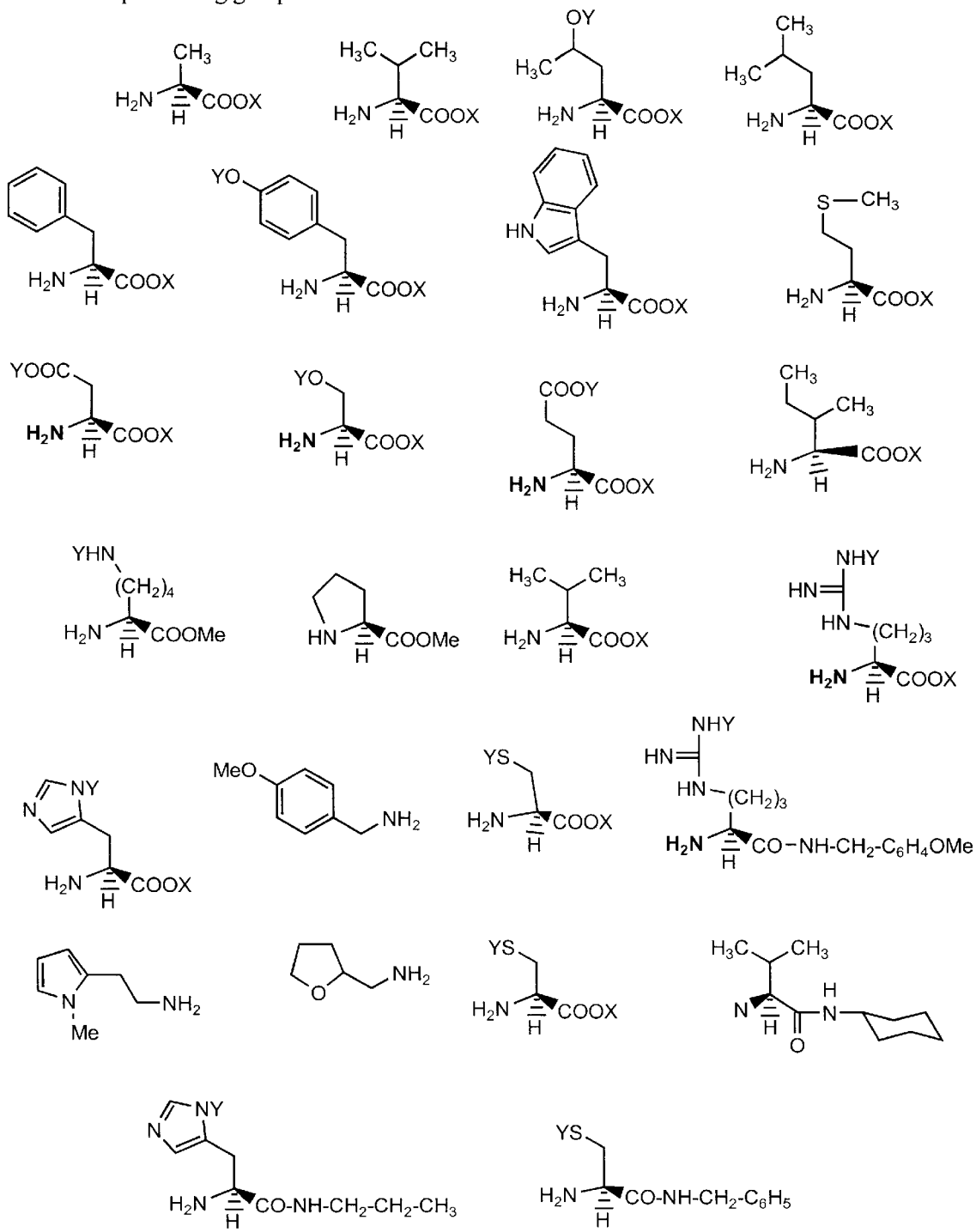
FIG. 2 shows exemplary amino acid and other primary amine-containing tool molecules for generating the combinatorial libraries of the invention.
Figure 3:
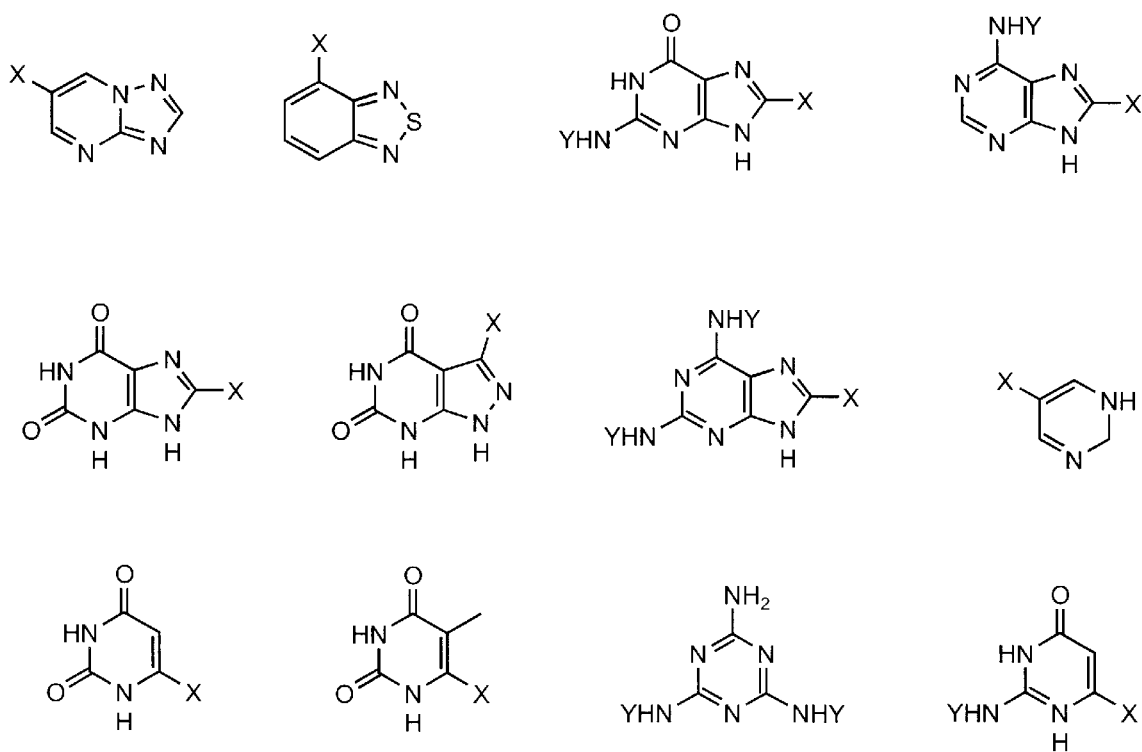
FIG. 3 shows exemplary nucleobase and modified nucleobase tool molecules for generating the combinatorial libraries of the invention.

Tool Molecule: refers to the different molecules having at least one functional group which reacts with the reactive centers of the core molecule s to form the combinatorial library molecules. Similar to libraries produced using recombinant methods (e.g., phage libraries containing recombinantly-produced peptides), the tool molecules of the invention can be the naturally-occurring L-amino acids or nucleobases (e.g., adenine, guanine, thymine, cytidine, uracil). In contrast to such recombinant libraries, the tool molecules also can be the non-naturally occurring molecules, such as a non-naturally occurring nucleobase, nucleoside or nucleotide analog, a D-amino acid, an L-amino acid analog, a non-naturally occurring carbohydrate (e.g., pentose and hexose sugar moieties) and carbohydrate analog. Examples of amino acids and other primary amines that are suitable for use as tool molecules are illustrated in FIG. 2. Examples of nucleobases and modified nucleobases that are suitable for use as tool molecules are illustrated in FIG. 3.

Functional Group: refers to a reactive group of the tool molecule which is capable of reacting with the reactive center of a core molecule to form a linkage. Preferably, the linkage is a covalent bond. For a linkage-forming reaction which follows a nucleophilic/electrophilic mechanism (discussed below), the functional group can be a nucleophile (e.g., an alcohol, an amine, a thiol) or an electrophile (e.g., an acid halide, an acyl halide). Thus, for a nucleophilic/electrophilic reaction mechanism, complementary pairs of reactive centers and functional groups (e.g., a nucleophilic reactive center and an electrophilic functional group, an electrophilic reactive center and a nucleophilic functional group) are selected to form the combinatorial libraries. Of course, other types of tool molecules (non-nucleophilic/non-electrophilic) can be reacted with the core molecules depending upon the type of mechanism employed for the coupling reaction (discussed below).

The tool molecules optionally include more than one functional group, e.g., a first functional group for reacting with the core molecule and a second functional group for reacting with a second molecule, such as a protecting group (described below).

Fixed Spatial Orientation: refers to the placement in space of at least two molecules (attached to the same molecule, such as a core molecule) relative to one another. In a most preferred embodiment, the core molecules of the invention include two or more reactive centers. The centers are positioned at a fixed spatial orientation relative to one another to permit attachment of two or more tool molecules at a fixed spatial orientation relative to one another. The phrase "fixed spatial orientation" embraces orientations which are entirely restricted in movement, as well as orientations which are partially restricted in movement such as in a library molecule in which the tool molecules on a core molecule are free to move within a limited sphere (e.g., to rotate about the linkage which attaches the tool molecule to the core).

Non-naturally occurring molecule: refers to a molecule which is not found in nature. Such molecules may be produced by synthetic or recombinant methods. For example, a non-naturally occurring peptide (i.e., a peptide which is not found in nature) can be prepared using recombinant methods (see, e.g., Pavia, M., et al., Bioorg. & Med. Chem. Ltrs. 3(3):387–396 (1993) or using chemical synthetic methods (see, e.g., Lam, K., et al., Nature 354:82–84 (1991)).

Protecting Group: refers to a material which is bound to a functional group or reactive center and which may be selectively removed therefrom to expose the functional group or reactive center in a reactive form. Preferably, the protecting groups are reversibly attached to the functional groups and can be removed (e.g., chemically or otherwise cleaved) from the functional groups and/or library molecules. The protecting groups include a hydrophobic moiety, which facilitates the separation of the unreacted core molecules and unreacted tool molecules from the combinatorial library molecules (discussed below).

Water-soluble/Fat-soluble: refers to the relative degree of solubility of a compound in an organic ("fat") phase or in an aqueous ("water") phase. A compound or molecule is said to be "fat-soluble" if it is more soluble in an organic phase than it is in an aqueous phase. A compound or molecule is said to be "water-soluble" if it is more soluble in an aqueous phase than it is in an organic phase.

Biologically-active/-inactive: refers to the functional activity of a molecule (e.g., ligate or ligand) or a structure (e.g., membrane). Different categories of ligates (described below) exhibit different functional activities. The following examples are illustrative only: The functional activity of a receptor ligate is the ability to specifically recognize and bind to a ligand. The functional activity of an antibody is the ability to specifically recognize and bind to an antigen, an antigenic determinant, or an epitope. The functional activity of an enzyme is the ability to catalyze a specific reaction. The functional activity of a nucleic acid is the ability to hydrogen bond to an oligonucleotide having a substantially complementary nucleic acid sequence. Some nucleic acids (e.g., ribozymes) also exhibit an enzymatic activity. Thus, for example, a library molecule is said to be biologically active if it has the ability to modulate the functional activity of a specific ligate or class of ligates. Different types of assays are necessary to screen the combinatorial libraries of the invention for the presence of biologically-active molecules.

Screening: refers to the process by which library molecules are tested for biological activity. For example, the ability to modulate the functional activity of a ligand or ligate can be used as a screening assay to identify lead compounds. A preferred screening method involves contacting the library with an immobilized ligate and identifying the library molecules which bind to the ligate. Alternatively, solution-phase competition assays can be used to screen combinatorial libraries (e.g., by contacting the library with an immobilized ligand in the presence of a soluble ligate for the ligand) and to assess the relative affinity of the library molecule for the ligate (Zuckermann, R., et al., *Proc. Natl. Acad. Sci. USA* 89:4505–4509 (1992)). Such assays are well known to those of ordinary skill in the art (see e.g., Lam, K., et al., supra. for a discussion of opiate peptide receptor assays). Other assays useful for identifying pharmaceutical and/or agricultural lead compounds include assaying for antimicrobial activity, assaying for antiviral activity (e.g., by measuring plaque inhibition) and assaying for anti-fungal activity.

Ligate: refers to a molecule that has an affinity for a ligand. Ligates may be naturally-occurring or non-naturally occurring and can be used in a soluble or an immobilized state, e.g., attached to a solid support. categories of ligates for which the combinatorial libraries of the invention are useful for identifying lead compounds include, but are not limited to, receptors, antibodies, enzymes and nucleic acids.

Receptor ligates: The preferred receptor ligates of the invention include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). Other receptors for which the combinatorial libraries are useful for identifying pharmaceutical lead compounds include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease).

Antibodies: The preferred antibody ligates of the instant invention include antibodies which recognize self-antigens such as those antibodies implicated in autoimmune disorders and antibodies which recognize viral (e.g., HIV, herpes simplex virus) and/or microbial antigens.

Enzymes: The preferred enzyme ligates of the instant invention include proteases (e.g., serine proteases such as trypsin and thrombin), polymerases (e.g., RNA polymerases, DNA polymerases), reverse transcriptases and kinases. Other enzymes for which the combinatorial libraries are useful for identifying pharmaceutical lead compounds include enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

Nucleic Acids: The preferred nucleic acid ligates of the instant invention include any segment of DNA or RNA containing natural or non-naturally occurring nucleosides. Nucleic acids are capable of specifically binding to other nucleic acids or oligonucleotides via complementary hydrogen-bonding and also are capable of binding to non-nucleic acid ligates. (See, e.g., Bock, L., et al., *Nature* 355:564–566 (1992) which reports inhibition of the thrombin-catalyzed conversion of fibrinogen to fibrin using aptamer DNA).

Ligand: refers to a molecule that is recognized by a ligate.

Lead Molecule: refers to a molecule which is capable of modulating the functional activity of a biological molecule. Screening assays are used to identify lead molecules in the combinatorial libraries of the invention. Examples of biological molecules for which lead molecules can be synthesized and selected in accordance with the invention include, but are not limited to, agonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

Analog: refers to a molecule which shares a common functional activity with the molecule to which it is deemed to be an analog and may share common structural features as well.

Pro-library: refers to a type of combinatorial library of molecules which may be further processed into another state to form a second combinatorial library. In a particularly preferred embodiment, the pro-library molecules contain protecting groups which enhance the fat-solubility of the library molecules. The pro-library is purified by extracting the water-soluble core and tool molecules from the fat-soluble pro-library molecules. The pro-library can be further processed by, for example, removing the protecting groups from the pro-library molecules, to yield a second combinatorial library which contains water-soluble molecules.

Enzyme Assays: The assays useful for identifying the protease inhibitors of the invention include, but are not limited to, the assays described in the U.S. patents identified below. The enzyme assays are useful for determining the inhibitory activity of the compounds produced using the process for creating molecular diversity disclosed herein.

U.S. Pat. No. 5,250.677: describes enzyme assays for measuring the catalytic activities of thrombin and trypsin in the presence and/or absence of a serine protease inhibitor.

U.S. Pat. No. 5,240,913: describes an alternative enzyme assay for measuring the catalytic activity of thrombin in the presence and/or absence of a serine protease inhibitor.

U.S. Pat. No. 5,192.668: describes an assay for determining the effect of a protease inhibitor on the enzymatic activity of a recombinant HIV protease.

U.S. Pat. No. 5,157.019: describes assays for measuring the catalytic activity of the following enzymes in the presence and/or absence of an enzyme inhibitor: elastase, cathepsin G, hemolytic factors, Factor C1, Factor D, thrombin, Factor $X_a$, plasma Kallikrein, plasmin, and tissue plasminogen activator (t-PA).

II. Introduction to the Preferred Embodiments

One method for forming a combinatorial library of the invention includes (a) admixing a plurality of core molecules, each having at least one reactive center with a plurality of different tool molecules, each having at least one functional group to form a reaction mixture; and (b) reacting the reactive centers of the core molecules with the functional groups of the tool molecules to form a combinatorial library of molecules. As used herein, the phrase "combinatorial library" refers to a collection of structurally-diverse molecules. As will be explained in more detail below, the extent of this diversity is dictated by the number, the nature and the ratio of the core molecules and tool molecules from which the library molecules are synthesized. Although the core molecules and tool molecules may have natural or synthetic origins, typically the product of the reaction between the core and tool molecules is a non-naturally occurring molecule. In the preferred embodiments, the library molecules have structures that are not recognized by degradative enzymes in vivo, a feature which contributes to the metabolic stability and improved absorption properties of these molecules in vivo.

The core molecules include at least one reactive center for reacting with the functional group of a tool molecule. Preferably, the core molecules serve as a rigid or relatively rigid scaffold to which tool molecules can be linked in a fixed spatial orientation relative to one another. Examples of core molecules that can be used in accordance with the methods of the invention, include, but are not limited to, the chemical compounds illustrated in FIG. 1 (e.g., monocyclic, polycyclic, heterocyclic and aromatic molecules). FIG. 1 illustrates two classes of core molecules: (1) rigid core molecules, exemplified by the planar aromatic and planar heterocyclic molecules shown in the figure and (2) relatively rigid core molecules, exemplified by the non-aromatic monocyclic and polycyclic molecules shown in the figure. The core molecules have a sufficiently rigid structure to maintain two or more tool molecules in a fixed spatial orientation relative to one another following covalent attachment of the tool molecules to the core molecule.

Examples of core molecules also include biochemical compounds (e.g., adenine, thymine, guanine, cytidine, uracil, inosine, as well as analogs, nucleosides, and nucleotides of the foregoing nucleobases). In a particularly preferred embodiment, the core molecules are pharmaceutical molecules having a known biological activity. Optionally, the pharmaceutical core molecules are derivatized (e.g., by converting a reactive center of the pharmaceutical core molecule into a more potent nucleophile or electrophile (discussed below) to enhance reaction of the core molecule with a tool molecule containing a complementary functional group. For example, a pharmaceutical core molecule having an antibiotic activity can be reacted with a plurality of tool molecules to form a library of derivatized antibiotic molecules. The derivatized pharmaceutical molecule library can be screened using well-known colony inhibition assays to identify lead compounds which, for example, exhibit enhanced antibiotic potency and/or which confer multidrug resistance. Conventional and/or novel separation techniques and analytical methods (e.g., HPLC and mass spectroscopy) can be used to elucidate the structure of the novel lead molecules. (See, e.g., the Examples).

The invention also embraces a method for forming a combinatorial library in which two or more different core molecules are reacted with a plurality of different tool molecules. As will be apparent to one of ordinary skill in the art, the inclusion of two or more different core molecules substantially increases the molecular diversity of the libraries formed in accordance with the methods of the invention.

In the preferred embodiments, the reactive centers of the core molecule form a covalent linkage with the functional groups of the tool molecules, although other types of linkages (e.g., a metal coordinate linkage in which a metal is used as the core molecule and the tool molecules form a coordinate bond to the metal, an ionic linkage) also fall within the scope of the invention. Although different types of reaction mechanisms (discussed below) can be used to form the combinatorial libraries of the invention, the preferred reaction forms a covalent linkage between the reactive centers of the core molecule and the functional group of the tool molecules. In general, almost any reaction for forming a covalent linkage can be used to link a tool molecule to a core molecule. For a summary of covalent coupling reactions, see, e.g., March, J., *Advanced Organic Chemistry*, 4th Ed., New York, N.Y., Wiley and Sons, 1985), pp.326–1120). The reactions for forming the following specific types of linkages are found in the March text at the pages indicated: (a) reaction of an alcohol and an acid chloride to form an ester bond (pp.346–347); (b) reaction of an alcohol and an alkyl chloride to form an ether bond (pp.342–343); (c) reaction of an amine and an acid chloride to form an amide bond (pp.370–371); and (d) reaction of an amine and an alkyl chloride to form a secondary amine (pp.364–366). Alternatively, covalent linkages can be formed using a palladium or other transition metal catalyzed coupling reaction (see, e.g., N. Miyaura, H. Suginome, and A. Suzuki, *Tetrahedron Ltrs*. 22:127–130 (1981)):

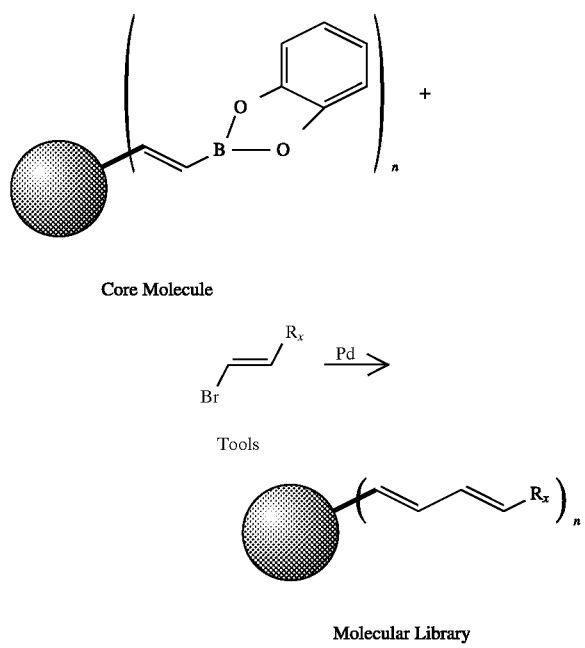

Core Molecule

Tools

Molecular Library

A particularly preferred reaction follows a nucleophile/electrophile mechanism for forming the covalent linkage between the core molecule and the tool molecule. As used herein, the terms "nucleophile" and "electrophile" have their common meanings (see, e.g., March, J., ibid.). In a nucleophilic/electrophilic reaction, one member of the complementary pair of reactants is an electrophile (such as a carbon atom of an activated carbonyl group) and the other member is a nucleophile (such as an alcohol, an amine or a thiol).

Figure 4:
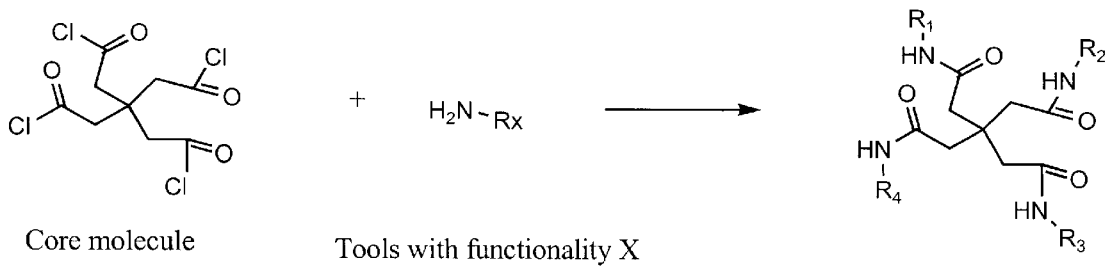
FIG. 4 schematically illustrates the reaction of an acid chloride reactive center with a primary amine functional group to form a library molecule containing an amide linkage.
Figure 5:
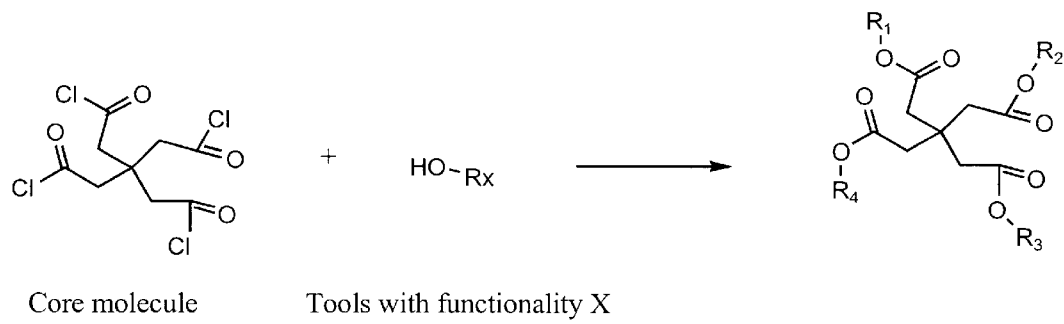
FIG. 5 schematically illustrates the reaction of an acid chloride reactive center with an alcohol functional group to form a library molecule containing an ester linkage.
Figure 6:
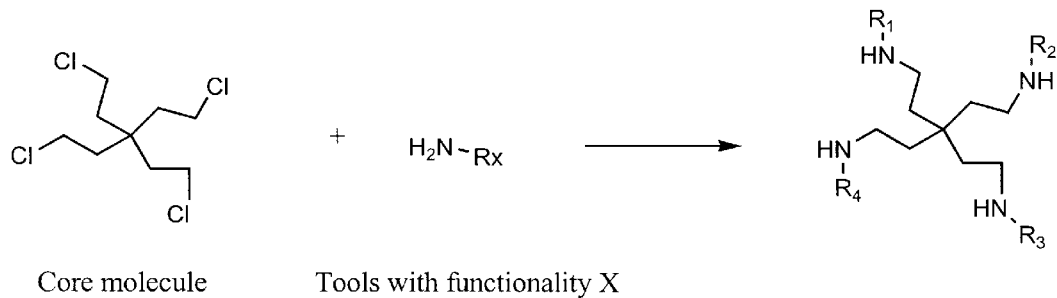
FIG. 6 schematically illustrates the reaction of an alkyl chloride reactive center with a primary amine functional group to form a library molecule containing a secondary amine linkage.
Figure 7:
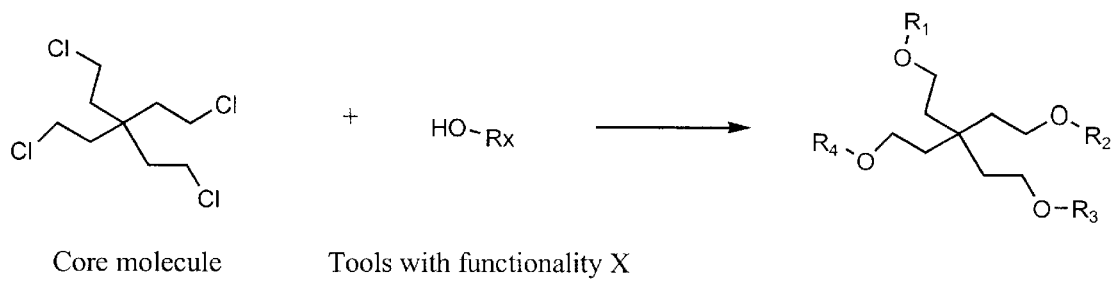
FIG. 7 schematically illustrates the reaction of an alkyl chloride reactive center with an alcohol functional group to form a library molecule containing an ether linkage.

For example, the core molecule can include one or more electrophilic reactive center(s) which react with a nucleophilic functional group of a tool molecule (described in more detail below) to form a library molecule in which the core molecule and the tool molecule are linked via a covalent bond. The core molecule can include an acid halide (e.g., an acid chloride) reactive center which is capable of reacting with a nucleophilic functional group, such as a primary amine or an alcohol, to form a library molecule in which the core molecule and the tool molecule are linked via an amide (FIG. 4) or an ester (FIG. 5) linkage, respectively. Likewise, the core molecule can include an alkyl halide (e.g., an alkyl chloride) reactive center which reacts with, for example, a primary amine or an alcohol, to form a library molecule including a secondary amine (FIG. 6) or ester linkage (FIG. 7), respectively.

Figure 8:
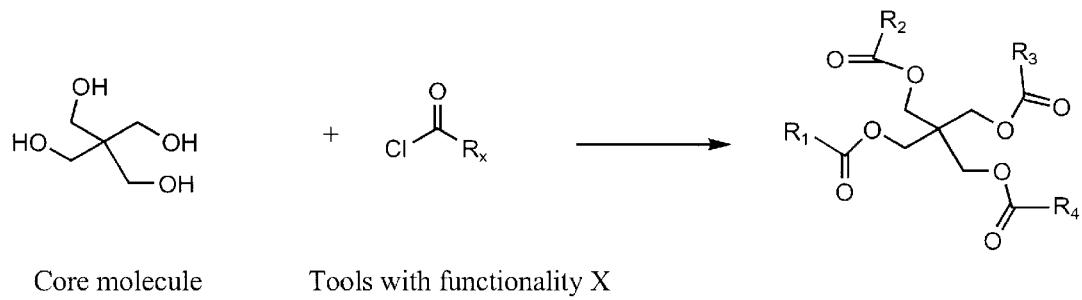
FIG. 8 schematically illustrates the reaction of an alcohol reactive center with an acid chloride functional group to form a library molecule containing an ester linkage.
Figure 9:
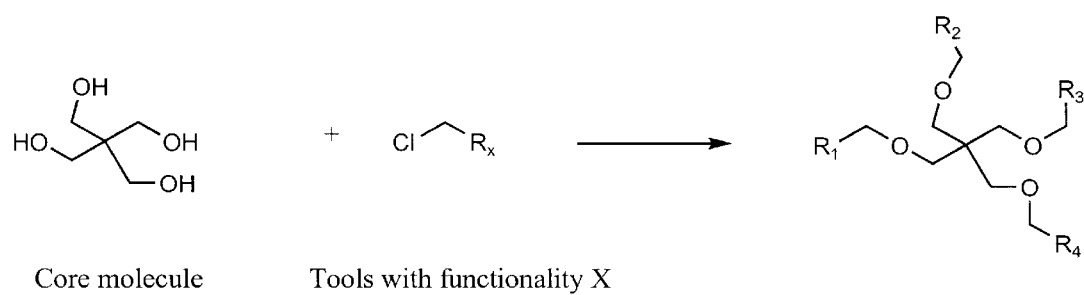
FIG. 9 schematically illustrates the reaction of an alcohol reactive center with an alkyl chloride functional group to form a library molecule containing an ether linkage.
Figure 10:
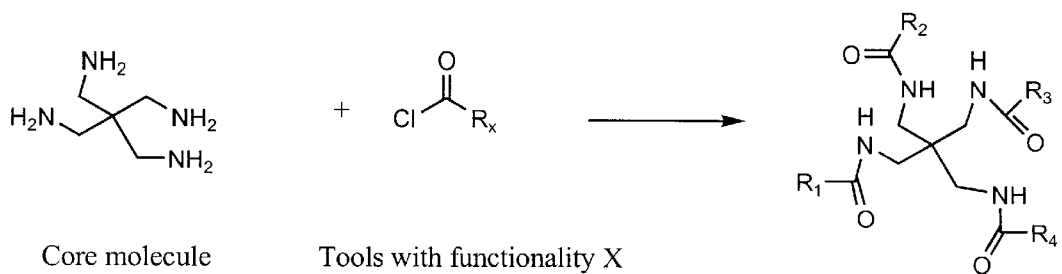
FIG. 10 schematically illustrates the reaction of a primary amine reactive center with an acid chloride functional group to form a library molecule containing an amide linkage.
Figure 11:
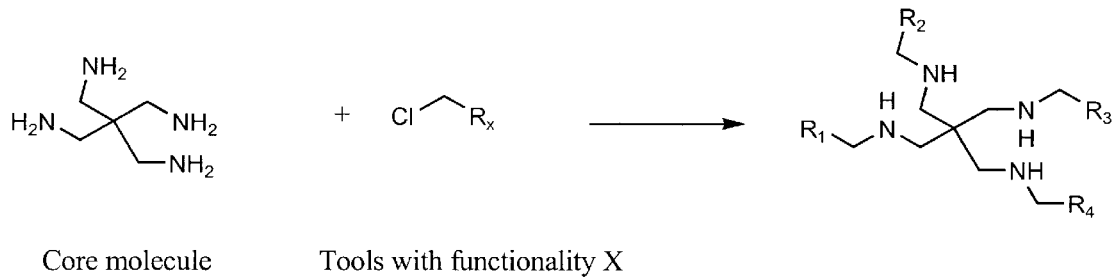
FIG. 11 schematically illustrates the reaction of a primary amine reactive center with an alkyl chloride functional group to form a library molecule containing a secondary amine linkage.

Alternatively, the core molecule can include one or more nucleophilic reactive center(s) which are capable of reacting with an electrophilic functional group of a tool molecule to form a library molecule in which the core molecule and the tool molecule are coupled via a covalent bond. For example, the core molecule can include an alcohol reactive center which reacts with an electrophilic functional group, such as an acid halide or an alkyl halide on a tool molecule, to form a library molecule in which the core molecule and the tool molecule are linked via an ester (FIG. 8) or an ether linkage (FIG. 9), respectively. Likewise, the core molecule can include a primary amine reactive center which, upon reaction with an acid chloride functional group or an alkyl halide, forms an amide linkage (FIG. 10) or a secondary amine linkage (FIG. 11), respectively.

Complementary pairs of core molecule reactive centers and tool molecule functional groups for generating combinatorial libraries are disclosed in Table 1. As illustrated in the table, exemplary reactive centers include, but are not limited to, an acid halide, an amine, an alcohol and a thiol. Other reactive centers and functional groups will be apparent to the artisan of ordinary skill in the art in view of the broad categories of reactive groups disclosed herein. In a particularly preferred embodiment, the reactive center is an acid chloride and the functional group of the tool molecule is an amine, an alcohol or a thiol group.

TABLE 1

COMPLEMENTARY PAIRS OF CORE MOLECULE REACTIVE CENTERS AND TOOL MOLECULE FUNCTIONAL GROUPS FOR GENERATING COMBINATORIAL LIBRARIES.

| Reactive Center on the Core Molecule | Functional Group on the Tool Molecule |
|---|---|
| R = core molecule | R = tool |
| R—COCl | R—OH RR'—NH RNH$_2$ R—SH R—COOH |
| R—X  R—CH$_2$—X  $\overset{O}{\underset{R}{\triangle}}$ <br> X = Cl, Br, I or leaving groups such as tosylate, mesylate, triflate | R—OH RR'—NH RNH$_2$ R—SH R—COOH <br> CH$_2$AB A,B = COR, COOR, <br> COOH, CN, NO$_2$ |
| R—⌬ | R—CH$_2$Hal R—Hal <br> R—COH R—COHal |

TABLE 1-continued

COMPLEMENTARY PAIRS OF CORE MOLECULE REACTIVE CENTERS AND TOOL MOLECULE FUNCTIONAL GROUPS FOR GENERATING COMBINATORIAL LIBRARIES.

| Reactive Center on the Core Molecule | Functional Group on the Tool Molecule |
|---|---|
| R—COH | RR'—NH RNH$_2$ R—C≡CH |
|  | R—CH$_2$Cl by Wittig reaction<br>CH$_2$AB A,B = COR, COOR,<br>COOH, CN, NO$_2$ |
| R—OH RR'—NH RNH$_2$ R—SH<br>R—COOH | R—COCl |
| R—OH RR'—NH RNH$_2$ R—SH<br>R—COOH | R—X  R—CH$_2$—X  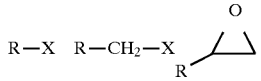<br>X = Cl, Br, I or leaving groups like tosylate, mesylate, triflate |
| R—CH$_2$Hal R—Hal<br>R—COH R—COHal | R—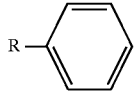 |
| RR'—NH RNH$_2$ R—C≡CH | R—CHO |
| R—CH$_2$Cl by Wittig reaction<br>CH$_2$AB<br>A,B = COR, COOR, COOH, CN,<br>NO$_2$ |  |

Exemplary tool molecules include, but are not limited to, the naturally-occurring nucleobases, nucleosides, nucleotides, oligonucleotides, amino acids, peptides and carbohydrates, as well as non-naturally occurring analogs of the foregoing molecules. Examples of amino acids and other primary amines that are suitable for use as tool molecules in the generation of combinatorial libraries are shown in FIG. 2. Examples of nucleobases and modified nucleobases that are suitable as tool molecules are shown in FIG. 3.

The tool molecules can be entirely or partly of synthetic origin. For example, the tool molecules (e.g., amino acids) can be purchased in their naturally occurring state (e.g., not derivatized) or in a derivatized state. In a particularly preferred embodiment, a plurality of amino acid tool molecules are derivatized (e.g., to attach a fat-soluble protecting group to a second functional group of the tool molecule) prior to reacting the tool molecule with a core molecule reactive center. (See, e.g., the Examples.)

The diverse tool molecules of the invention have in common a functional group which is capable of reacting with a reactive center of the core molecule to form a linkage. In general, the same coupling reaction conditions can be used to react any electrophile (e.g., an acyl halide, an alkyl halide) with any nucleophile to covalently couple the electrophile-containing molecule (e.g., the core) to the nucleophile-containing molecule (e.g., the tool). However, the incubation times for completing the coupling reaction will vary depending on the reactivity of the particular complementary nucleophile/electrophile pair participating in the reaction. Thus, for example, a strong nucleophile (e.g., an amine) will react with a strong electrophile (e.g., an acyl chloride) to form an amide linkage in less than thirty minutes using the reaction conditions provided in the Examples. In general, a longer incubation time or an increase in the incubation temperature (e.g., from room temperature to 40° C.) can be used to enhance the reactivity of a weak nucleophile/electrophile pair. The optimization of reaction conditions for each complementary pair of electrophiles and nucleophiles is within the ordinary skill of the art.

Preferably, the tool molecules that are used to form the combinatorial library include more than one functional group, e.g., a first functional group for reacting with the core molecule and a second functional group for reacting with a second molecule, such as a protecting group, to form a second linkage. Accordingly, in a particularly preferred embodiment, a method for forming a combinatorial library further includes the step of reacting the secondary functional group with a protecting group prior to admixing the plurality of core molecules with the plurality of tool molecules. A particularly preferred procedure for synthesizing a protecting group-derivatized amino acid tool molecule (in which the protecting group is covalently coupled to an amino acid side chain functional group) is provided in the Examples. Exemplary protecting groups which can be cleaved from the library molecules under strongly acidic conditions ("acid sensitive protecting groups") or basic conditions ("base sensitive protecting groups") are listed in Table 2. A fatty acid also may serve as a removable protecting group, e.g., a fatty acid coupled to a tool molecule via an ester linkage nay be cleaved from the tool molecule upon exposure to aqueous basic conditions.

TABLE 2

PROTECTING GROUPS THAT CAN BE CLEAVED FROM FUNCTIONAL GROUPS

| Functional Group | Protecting Group | |
|---|---|---|
| Acid Sensitive protecting groups: | | |
| OH | t-Bu | (tertiary butyl ether) |
| COOH | Ot-BU | (tertiary butyl ester) |

TABLE 2-continued

PROTECTING GROUPS THAT CAN BE CLEAVED FROM FUNCTIONAL GROUPS

| Functional Group | Protecting Group | |
|---|---|---|
| NH2 | BOC | (tertiary butyloxycarbonyl) |
| Guanidine | MTR | (4-Methoxy-2,3,6-trimethyl-benzene-sulfonyl) or |
| | PMC | (2, 2, 5, 7, 8-Pentamethychroman-6-sulfonyl) |
| Histidine | Trt | (Triphenylmethyl) |
| SH | Trt | (Triphenylmethyl) |
| Base Sensitive protecting groups: | | |
| NH2 | FMOC | (fluorenylmethoxycarbonyl |

The protecting group primarily serves to modulate the solubility properties of the protecting group-derivatized tool molecule and the library molecules formed therefrom. For example, the reaction of a core molecule (having a hydrophilic acid chloride reactive center) with a lysine tool molecule (in which a fat-soluble, protecting group is covalently linked to the epsilon amine group) yields a library molecule in which the core molecule and the tool molecule are coupled via an amide bond, i.e., the hydrophilic groups of the core and tool molecule are not available to enhance the water-solubility of the library molecule. This difference in solubility allows the fat-soluble, protecting group-derivatized library molecules to be separated from the unreacted core molecules and unreacted tool molecules by extracting the core and tool molecules into an aqueous phase while the library molecules remain soluble in the organic phase. If, however, the lysine tool molecule portion of the library molecule contains an unprotected amine functional group, the library molecule amine group will be protonated under the extraction conditions used to remove the core and tool molecules and the separation procedure will be made substantially more difficult.

In general, a combinatorial library is generated by loading a plurality of core molecules, a plurality of different tool molecules and 5 ml of dichloromethane (or other solvent in which the core molecules and tool molecules are soluble) into a round bottom flask equipped with a magnetic stir bar. The addition of base to the reaction mixture in the flask (typically about 1 ml triethylamine) starts the coupling reaction, which then is allowed to continue for 1 to 24 hours (depending on the reactivities of the particular electrophiles/nucleophiles present in the reaction) at room temperature under an argon atmosphere.

In general, the amounts of core molecules and tool molecules used in the coupling reaction are selected so that the molar ratio of tool molecule functional groups to core molecule reactive centers is slightly greater than, or equal to, 1. This selection criterion enhances the likelihood that each core reactive center will be linked to a tool molecule and that each tool molecule (regardless of whether it contains a strong or a weak electrophilic or nucleophilic functional group) will react with a core molecule reactive center. For example, the optimum total moles of a plurality of amino acid tool molecules (assuming each amino acid has a single functional group) that should be reacted with 10 moles of a core molecule having 4 reactive centers is slightly greater than, or equal to, 40 (because there are 40 moles reactive centers in the reaction mixture). If the molar ratio of tool molecule functional groups to reactive centers is significantly greater than 1.0, the diversity of the combinatorial library may be limited because only the most reactive functional groups will react with the reactive centers. If the molar ratio of tool molecule functional groups to reactive centers is less than 1.0, the combinatorial library molecules may include unreacted reactive centers which will likely exhibit similar solubility properties as the unreacted core molecule and extraction of the unreacted core molecules likely will be more difficult. In this manner, libraries have been generated in which each member of the library is present in the library at the same approximate concentration (preferably within 20%, more preferably within 10%) as any other member of the library. In a particularly preferred embodiment, each library contains at least about 100 different compounds. More preferably, the library contains at least about 100 different members with each member present in the library at the same approximate concentration as any other member of the library.

A particularly preferred procedure for separating the unreacted tool molecules and core molecules from the library molecules, based upon the solubility differences between the unreacted molecules and the library molecules, is described herein. Following completion of the coupling reaction, unreacted core molecules, unreacted tool molecules and library molecules containing core molecules coupled to one or more tool molecules are dissolved in approximately 50 ml of an organic solvent (preferably dichloromethane). The addition of a weak acid (e.g., 1M citric acid) to the organic phase protonates the amine functional group of each unreacted tool molecule to form a quaternary amine, thereby rendering the tool molecules soluble in the weak acid (and insoluble in the dichloromethane). Accordingly, in a particularly preferred embodiment, the unreacted tool molecules are extracted from the organic phase by washing the organic phase with two 75 ml washes of a 1M citric acid solution.

Exposure to citric acid also results in converting the acid chloride reactive center of each core molecule into its corresponding free acid (which remains soluble in the organic phase). The addition of a weak base (e.g., 100 ml of saturated sodium hydrogen carbonate solution) to the organic phase deprotonates the unreacted core molecule acid moiety (i.e., the core molecule now carries a negative charge), thereby rendering the unreacted core molecules soluble in the weak base but insoluble in the organic phase and allowing extraction of the unreacted core molecules. After removal of the weak base solution, the organic phase (containing the pro-library) is dried over $MgSO_4$ to remove trace amounts of aqueous phase and is concentrated to yield an oil. The oil comprising the fat-soluble pro-library is dried under high vacuum to yield a foam which can be screened directly for the presence of a lead compound or which can be processed into a second, water-soluble library prior to screening.

In the preferred embodiments, the fat-soluble pro-library is converted into a water-soluble library-by removing the protecting groups from the pro-library molecules (e.g., by chemically cleaving the protecting groups from the molecules under acidic or basic conditions, see Table 2). Because of its solubility properties, the fat-soluble pro-library is useful for identifying pharmaceutical lead compounds which modulate, for example, membrane-associated biological processes. Removal of the fat-soluble protecting group from the pro-library molecules yields a library of water-soluble molecules which is useful for identifying pharmaceutical lead compounds that modulate aqueous biological processes. Accordingly, to identify lead molecules which modulate aqueous biological processes, the method for forming a combinatorial library further includes the step of converting the fat-soluble pro-library into a biologically-active state, e.g., by removing the fat-soluble protecting groups from the pro-library molecules (as described above)

or by derivatizing the fat-soluble library molecules to render them water-soluble.

Because the principle utility of the invention is the generation of combinatorial libraries for the identification of pharmaceutical and/or agricultural lead compounds, the methods of the invention further include the step of screening the combinatorial libraries for biologically-active molecules. Numerous screening methods have been reported for identifying lead compounds which modulate the activity of a particular ligate. Such methods include selecting the library molecules which bind to an immobilized ligate (e.g., an antibody), selecting molecules which compete with a soluble ligand for binding to an immobilized or membrane-associated ligate (e.g., a receptor) and selecting molecules which modulate the activity of the ligate (e.g., an enzyme, a microbe, a virus) in a dose-dependent manner. For example, molecules having antimicrobial activity and/or antiviral activity can be identified using well-known colony inhibition or plaque inhibition assays, respectively. Following identification of a fraction containing one or more lead compound(s), conventional and/or novel separation techniques and analytical methods (e.g., HPLC and mass spectroscopy) are used to elucidate the structure of the novel lead molecule. (See, e.g., the Examples).

As will be apparent to the artisan of ordinary skill in the art, the extent of molecular diversity of the libraries described herein is delineated by several variables: (1) the number of reactive centers per core molecule; (2) the number of different types of core molecules; (3) the number of functional groups per tool molecule; (4) the number of different tool molecules; and (5) the ratio of tool molecules to core molecules. The dependence of molecular diversity upon these variables is illustrated in the following example.

The generic formula for the reaction of a core molecule having n reactive centers with x different tool molecules, each tool molecule including at least one functional group, is represented by the equation:

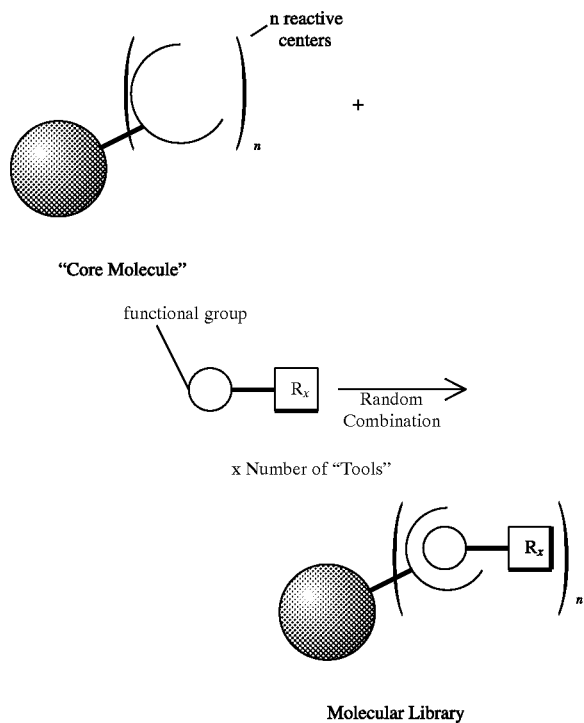

The reaction yields a molecular library which has diversity, the extent of which is, at least in part, defined by the values of n and X. By selecting a particular set of different tool molecules (e.g., a set of amino acids or peptides, a set of nucleosides or oligonucleotides, a set of tool molecules including a mixture of both amino acids and nucleosides), combinatorial libraries containing molecules having the potential to bind to a particular type of ligate (e.g., an amino acid-binding ligate, nucleoside-binding ligate) are generated.

According to related aspects of the invention, an automated process for generating the combinatorial libraries of the invention, as well as the equipment for performing the automated process, also are provided. In view of the simplicity of the reactions disclosed herein and the state of the art with respect to the automation of more complex methods for generating combinatorial libraries, automation of the processes disclosed herein is enabled by the instant disclosure (see, e.g., Pavia, M., et al., supra.; Jung, G. and Beck-Sickinger, A., *Angewandte Chemie* (*Intl. Ed. in Enc.*) 31(4):367–486 (1992) for a discussion of fully automated peptide synthesizers and Zuckermann, R., et al., supra. for a description of the robotic synthesis of peptide mixtures).

According to still another aspect of the invention, a fat-soluble combinatorial pro-library of non-naturally occurring molecules is provided. The library molecules include at least one tool molecule linked to a core molecule. In the preferred embodiments, the tool molecules further include a removable, fat-soluble protecting group. The fat-soluble pro-library is useful for identifying pharmaceutical and/or agricultural lead compounds which modulate organic phase-associated biological processes. Optionally, the pro-library can be further processed into a water-soluble library that is useful for identifying pharmaceutical and/or agricultural lead compounds which modulate aqueous-associated biological processes.

According to another aspect of the invention, a molecular library containing a plurality of non-naturally occurring molecules is provided. Each molecule includes a first tool molecule and a second tool molecule covalently coupled to a core molecule. The first and second tool molecules are positioned at a fixed spatial orientation relative to one another. Combinatorial libraries which differ solely in the spatial orientation of the first and second tool molecules are useful for identifying the optimal spatial orientation between tool molecules for binding to a particular ligate. For example, a first library can be generated by reacting a first core molecule (having reactive centers positioned at a first spatial orientation) with a plurality of tool molecules to form a first combinatorial library. A second combinatorial library can be generated by reacting a second core molecule (having reactive centers positioned at a second spatial orientation) with the same plurality of tool molecules used to generate the first combinatorial library. Each library is screened to identify a lead compounds) and the relative biological activities of the lead compound(s) present in the first and second libraries are compared. A comparison of the biological activities for the lead compounds found in each library makes it possible to optimize the spatial orientation of the lead molecules for optimum binding to a particular ligate.

Also within the scope of the invention are kits for forming a combinatorial library. The kits contain a plurality of core molecules, each having at least one reactive center and instructions for reacting the core molecules with a plurality of tool molecules to form a combinatorial library. Preferably, the plurality of tool molecules are included in the kit. More preferably, the kits contain separate pluralities of core molecules which differ from one another in the nature and/or spatial orientation of the core reactive centers. The kits are useful for generating more than one combinatorial library which differ in the type (e.g., amide, aldehyde) and/or spatial orientation of the linkage connecting the core and tool molecules.

According to yet another aspect of the invention, a combinatorial library including a plurality of non-naturally occurring molecules is provided. The library molecules include at least one tool molecule that is covalently coupled to a xanthene molecule. In a particularly preferred embodiment, the tool molecules are selected from the group consisting of amino acids and nucleosides. Specific reactions for preparing the particularly preferred amino acid-derivatized xanthene molecules are disclosed in the Examples.

The utilities of the invention include the identification of novel pharmaceutical and/or agricultural lead compounds which antagonize, agonize or otherwise modulate the physiological activity of natural ligands. Thus, the libraries disclosed herein contain compounds which have the potential to modulate the functional activity of biological processes implicated in (but not limited to) disease progression, immune system modulation, and neurological signal transmission. The libraries of potential lead compounds include compounds which mimic the active determinants (i.e., the ligate-binding portion of the molecule) on hormones, cytokines, enzyme substrates, enzyme cofactors, virus, microbes and fungi. The combinatorial libraries of the invention also are potentially rich sources of novel antimicrobial, anti-viral and anti-fungal agents.

In view of the state of the art with respect to the use of combinatorial libraries for epitope mapping (see e.g., Jung, G. and Beck-Sickinger, A., supra. which reports the epitope mapping of the immunogen region of cytomegalovirus (hCMV) using a library of 49 peptides simultaneously prepared on cellulose paper sheets), use of the combinatorial libraries disclosed herein for epitope mapping is supported by the instant disclosure and is within the skill in the art. Accordingly, the libraries are useful for identifying the epitopes of numerous types of ligands and ligates (e.g., receptors, antibodies, enzymes, nucleic acids, carbohydrates, lipids), including both continuous epitopes (i.e., the epitope is formed of contiguous molecules) and discontinuous epitopes (i.e., the epitope is formed by the juxtaposition of non-adjacent ligand monomers as a result of, for example, secondary/tertiary structure folding). The majority of naturally-occurring ligates are believed to recognize discontinuous epitopes (Pavia, M., et al., supra.).

According to one aspect of the invention, an isolated compound of the formula (hereinafter "Formula I"):

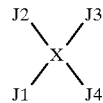

is disclosed. As used herein, "isolated" in reference to a compound refers to a compound which, by virtue of its origin or manipulation, is not associated with other molecules with which it shares common structural elements. Thus, for example, isolated compounds include compounds which have been chemically synthesized alone or as one component of the molecular libraries described herein and which have been purified from a more complex mixture of molecules (such as a mixture containing the reactants from which the compound was synthesized or such as a library from which the molecule was removed by, for example, affinity chromatography). Regardless of its origin (i.e., separately synthesized or synthesized during generation of a molecular library), a compound is an "isolated compound" when it is no longer present in a mixture containing compounds with which it shares common structural elements (e.g., common core molecules and/or common tool molecules). A "substantially isolated" compound refers to a compound which, although associated in a mixture with compounds with which it shares common structural elements, represents at least about 10% of the compounds present in the mixture. The substantially isolated compounds of the invention exhibit a detectable (i.e., a statistically significant) protease inhibition activity (anti-protease activity) when tested in conventional protease assays such as those described above.

The compounds of the invention include a core molecule, "X", to which is covalently attached each of four tool molecules (J1, J2, J3 and J4) at a fixed spatial orientation relative to one another. In a particularly preferred embodiment, each tool molecule is attached to the core molecule via an amide linkage. The isolated compound exhibits an anti-enzyme activity, i.e., the compound reduces or eliminates the catalytic activity of an enzyme. Anti-enzyme activities are detected by performing enzyme assays in the presence and absence of a putative enzyme inhibitor (anti-enzyme) and determining whether the putative inhibitor specifically inhibits the catalytic activity of the enzyme. An exemplary procedure for identifying an anti-trypsin compound present in a molecular library is provided in Example 11. An exemplary prophetic example for identifying additional compounds having anti-serine protease activities is provided in Example 13. Exemplary serine proteases that can be assayed in accordance with the methods described herein in order to identify serine protease inhibitors, include trypsin, thrombin, chymotrypsin, elastase, subtilisin and Factor Xa. (See, e.g., *Enzyme Structure and Mechanism*, 2nd edition, A. Fersht, ed., W. H. Freeman and Co., N.Y., N.Y. (1984) for a discussion of serine proteases and their mechanism of action).

Core molecule "X" is xanthene or a "xanthene spatial analog", i.e., a molecule that maintains the tool molecules at approximately the same fixed spatial orientation that would result had the tool molecules been covalently attached to xanthene positions 2, 4, 5 and 7. Exemplary xanthene spatial analogs include naphthalene, anthracene, benzene and other planar aromatic heterocyclics. In a preferred embodiment, the core molecule is xanthene and tool molecules J1, J2, J3 and J4 are covalently coupled to xanthene at xanthene positions 2, 4, 5 and 7, respectively.

In a particularly preferred embodiment, tool molecules J1 and J3 are of the formula (hereinafter "Formula II"):

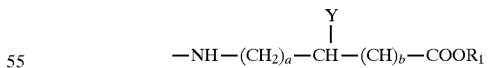

wherein Y can be a branched chain hydrocarbon group containing 1 to 7 carbon atoms, each of a and b is 0 to 2, and $R_1$ is selected from the group consisting of hydrogen (a free acid), an alkyl group containing 1 to 7 carbon atoms (an ester), an aryl group (an ester), and an alkylaryl group containing 6 to 14 carbon atoms (an ester). Tool molecules J1 and J3 can be the same or different; Numerals a and b can be the same or different. In a preferred embodiment, each of J1 and J3 is an L-amino acid with a branched, hydrophobic side chain (e.g., L-Val or L-Ile, or a derivative thereof, such as L-valine methyl ester, L-Ile methyl ester).

Preferably, tool molecule J2 is of the formula (hereinafter "Formula III"):

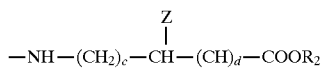

wherein Z is a hydrocarbon spacer containing 1 to 7 carbon atoms and a "proton accepting group", each of c and d is 0 to 2 and $R_2$ is selected from the group consisting of hydrogen, an alkyl group containing 1 to 7 carbon atoms, an aryl group and an alkylaryl group containing 6 to 14 carbon atoms. Spacer Z can be saturated or unsaturated and optionally, may include an ether linkage, e.g., Z=$NH_2$—$CH_2$—$CH_2$—O—$CH_2$—CH—. As used herein, "proton accepting group" refers to a group that contains a basic electron pair. Thus, proton accepting groups are protonated in water. The preferred J2 tool molecule is an L-amino acid with a basic side chain, e.g., L-Lys, L-Arg, a derivative of L-Lys (e.g., L-Lys methyl ester) or a derivative of L-Arg (L-Arg methyl ester). In a particularly preferred embodiment, the J2 tool molecule is L-Lys methyl ester.

Preferably, tool molecule J4 is of the formula (hereinafter "Formula IV"):

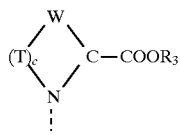

wherein each of T and W are selected from the group consisting of a carbon atom and an oxygen atom, e is 1 to 3 and $R_3$ is selected from the group consisting of hydrogen, an alkyl group containing 1 to 7 carbon atoms, an aryl group, and an alkylaryl group containing 6 to 14 carbon atoms. Preferably, J4 is L-Pro or a derivative of L-Pro such as L-Pro methyl ester.

The $R_1$, $R_2$ and $R_3$ groups of the J1, J2, J3 and J4 tool molecules can be the same or different. However, it is preferred that at least one of the above-identified R groups be hydrogen to result in a compound having at least one free acid, thereby enhancing its solubility in water. Whole numbers a, b, c, d and e can be the same or different. T and W also can be the same or different.

According to one embodiment, the serine protease inhibitor includes a xanthene core molecule, a J1 tool molecule that is L-Val or L-Ile (or a derivative of L-Val or L-Ile), a J2 tool molecule that is a basic L-amino acid, e.g., Lys, Arg (or a derivative of Lys or Arg), a J3 tool molecule that is L-Val or L-Ile (or a derivative of L-Val or L-Ile), and a J4 tool molecule that is L-Pro (or a derivative of L-Pro). More preferably, J2 is L-Lys methyl ester. In the most preferred embodiment, the serine protease inhibitor exhibits anti-trypsin activity and includes a xanthene core molecule to which L-Val (J1), L-Lys methyl ester (J2), L-Ile (J3) and L-Pro (J4) are covalently attached at xanthene positions 2, 4, 5 and 7, respectively. This compound (having Formula V) was identified in a complex molecular library using the iterative screening procedure described in Example 11.

Synthesis and characterization of the compound of Formula V with respect to its ability to inhibit the catalytic activity of trypsin in the spectrophotometric assay described in Example 11, demonstrates the utility of the process for creating molecular diversity disclosed herein for identifying novel lead compounds. In view of the above-summarized literature and patents which evidence the use of trypsin inhibitors for facilitating the culture of adherent cells (Example 12) and for treating physiological conditions caused by abnormally elevated serine protease levels, the usefulness of the novel serine protease inhibitors disclosed herein would be immediately apparent to one of ordinary skill in the art. (See, e.g., Sigma Chemical Co., catalog, St. Louis, Mo.; U.S. Pat. No. 5,250,677; and U.S. Pat. No. 5,109,018).

The serine protease inhibitors of the invention also are useful for preventing undesired proteolysis by a serine protease of a valuable peptide and/or protein substrate (hereinafter "protease target"). One method for preventing such undesired proteolysis involves contacting a preparation containing the peptide and/or protein with an effective amount of a serine protease of the invention to inhibit the enzymatic activity of the serine protease in vitro. In a particularly preferred embodiment, the compound of Formula V is contacted with the preparation. Thus, for example, the inhibitors of the invention can be added to preparations containing antibodies, enzymes, plasma proteins, tissue extracts, or other peptides and/or proteins which are used, e.g., in clinical analysis and biomedical research, to prevent the undesired proteolysis of the peptide and/or protein protease targets.

For in vitro use, the inhibitor(s) of the invention typically are dissolved in an organic solvent such as dimethylsulfoxide and are added to an aqueous solution containing the protease target(s) such that the final concentration of organic solvent is 25% or less. Typically, the solution is centrifuged to obtain a clear solution for use as an enzyme inhibitor. Alternatively, the inhibitors may be added to the preparation as a solid or in a suspension. As would be apparent to one of ordinary skill in the art, the solubility in aqueous solution of an inhibitor of Formula I is, at least in part, dependent upon the nature of tool-molecules J1, J2, J3 and J4. In general, tool molecules which include a free acid (i.e., $R_1$, $R_2$ and/or $R_3$ are hydrogen) will confer greater solubility (in aqueous solution) upon the inhibitor than tool molecules for which $R_1$, $R_2$ and/or $R_3$ are not hydrogen.

One or more serine protease inhibitors of the invention (preferably inhibitors of Formula V, and/or other protease inhibitors having a $K_i$ (inhibition constant) of at least $10^{-4}$M are selected as lead molecules for further study. In general, promising lead molecules (e.g., molecules which can be further modified to result in a clinically useful drug) have $K_i$ values between about 10 $\mu$M to 100 $\mu$M. Preferably, inhibitors that are intended as pharmaceutical agents have $K_i$ values between about $10^{-6}$M and about $10^{-10}$M.

One or more serine protease inhibitors of the invention (preferably inhibitors of Formula V, and/or other protease inhibitors having a $K_i$ (inhibition constant) of at least about $10^{-6}$M are formulated into a pharmaceutical composition by placing the inhibitor in a "pharmaceutically acceptable carrier". Exemplary formulations of synthetic protease inhibitors are disclosed in U.S. Pat. No. 5,109,018, the contents of which have been incorporated herein by reference. The pharmaceutical composition is prepared by placing a therapeutically effective amount of any of the serine protease inhibitors of the invention in a pharmaceutically acceptable carrier. As used herein, a "therapeutically effective amount" is that amount which is capable of preventing, alleviating and/or halting further progression of the symptoms associated with the physiological condition that is attributable to the abnormally elevated level of serine protease activity in vivo. As used herein an "abnormally elevated level" (in reference to serine protease activity) is an increase in the amount of serine protease activity that is statistically significant (with respect to the amount of serine protease activity that is found in a normal subject, i.e., a subject having a level of protease that is not associated with an adverse physiological condition such as emphysema, pancreatitis).

One method of the invention involves administering a pharmaceutical composition containing a therapeutically effective amount of an isolated serine protease inhibitor of the invention to a subject diagnosed as having a physiological condition caused by an abnormally elevated level of a serine protease. Optimal dosages and regimens for administering the protease inhibitors of the invention to a given subject can be readily ascertained by those of ordinary skill in the art. In general, such doses will vary depending upon the particular composition formulated, the mode of administration and the particular host and condition being treated. Factors that influence the action of the protease inhibitor include age, weight, sex, diet, time of administration, route of administration, condition of patient, drug combinations, reaction sensitivities and the severity of the condition being treated. (See also U.S. Pat. No. 5,250,677 for a discussion of the variables that may influence the effective amount of a synthetic, non-peptide protease inhibitor administered to a subject).

In general, the therapeutically effective amount will be between about 1 ug and about 100 mg/kg, more preferably between about 0.2 mg and about 100 mg/kg. The protease inhibitor(s) of the invention is formulated into a pharmaceutical composition by combination with an appropriate pharmaceutically acceptable carrier. For example, the protease inhibitors may be used in the form of their pharmaceutically acceptable salts, or may be used alone or in appropriate association, as.well as in combination with other pharmaceutically active compounds. The protease inhibitors may be formulated into preparations in solid, semisolid, liquid or gaseous form such as tablets, capsules, powders, granules, ointments, solutions, suppositories, and injections, in usual ways for oral, parenteral, or surgical administration. Exemplary pharmaceutically acceptable carriers are described in U.S. Pat. No. 5,211,657.

Exemplary physiological conditions caused by an abnormally elevated level of one or more serine proteases are described in U.S. Pat. Nos. 5,109,018 ("Powers et al. '018") and 5,250,677 (Han '677"), the contents of which patents have been incorporated herein by reference. In particular, Powers '018 describes the use of heterocyclic compounds in inhibiting serine proteases with chymotrypsin-like, elastase-like and trypsin-like specificity for treating diseases which involve destruction of tissue by serine proteases (e.g., pancreatitis, emphysema, rheumatoid arthritis, adult respiratory distress syndrome and other inflammatory conditions). The utility of trypsin inhibitors for treating pancreatitis also has been demonstrated by Sobajima et al. who report a synthetic trypsin inhibitor (4-(2-succinimidoethylthio)-phenyl 4-guanidinobenzoate methane sulfonate) for treating severe acute pancreatitis in a rat model (Sobajima, H., et al., Digestion 55(2):90–96 (1994), the contents of which are incorporated herein by reference).

These and other representative utilities of the invention are illustrated in the following non-limiting Examples. The present invention provides methods for forming combinatorial libraries of molecules which are useful for identifying pharmaceutical and/or agricultural lead compounds. The following Examples illustrate a particularly preferred embodiment of the method and representative utilities of the present invention.

EXAMPLES

The disclosure of the present invention illustrates the reaction of a number of different core molecule/tool molecules combinations. According to one embodiment, a plurality of core molecules (xanthene-di-acid chloride) having two reactive centers (n=2) was reacted with ten different tool molecules to form a combinatorial library. Because each tool molecule included a single amine functional group (i.e., X=10), the library theoretically contained fifty-five different library molecules. Preparative HPLC separation, combined with fast atom bombardment mass spectrometry, demonstrated that at least 41 different library molecules (or about 75% of the theoretical value) were formed.

More complex combinatorial libraries also have been prepared by reacting a plurality of core molecules (xanthene-tetra-acid chloride) having four reactive centers (n=4) with 4 (FIG. 12), 7 (FIG. 13), 12 (FIG. 14) or 21 (FIG. 15) different tool molecules (each including a single amine functional group). A proportional increase in molecular diversity for libraries formed by reacting increasing numbers of different tool molecules with a constant number of core molecules was demonstrated using high pressure liquid chromatography (HPLC) and mass spectroscopy. Theoretically, the reaction of one core molecule (including four reactive centers) with twenty-one different tool molecules yielded a library containing 97,461 different molecules. Although the exact numbers of library molecules formed could not be determined from the HPLC results, the HPLC elution profile (FIG. 15) demonstrated the presence of substantial diversity in this library.

Materials and Methods:

Amino acids were purchased from Nova Biochem, La Jolla, Calif. FMOC-derivatized amino acids were purchased from Advanced Chemtech.Inc., Louisville, Ky.

Solvents, acids and bases were purchased from Fluka Chemie, Ag, Buchs, Switzerland, unless otherwise noted.

Reagent grade solvents were used throughout the procedure unless otherwise noted.

HPLC Chromatography was performed using a silica column (preparative or analytical, as described below) on a Waters 600E HPLC System with a Waters 490E UV detector (UV detection at 270 nm) and a Waters 717 autosampler (Millipore Corp., Waters Chromatography Division, Milford, Mass.). The gradient used was threefold: 100% hexane to 100% ethyl acetate to 6% methanol/94% ethyl acetate. All HPLC solvents were purchased from EM Science (Gibbstown, N.J.) and were EM Science's Omni Solve® grade. The analytical silica column was purchased from Beckman Instruments, Inc., Fullerton, Calif. (part #235341, ULTRASPHERE® SI column, 4.6 mm i.d.×25 cm length, 80 angstrom, 5 micrometer). The preparative silica column was purchased from Millipore, Waters Chromatography Division, Milford, Mass. (part #25823, NOVA PAK® HR silica, 19 mm i.d.×30 cm length, 68 angstrom, 6 micrometer).

Samples were analyzed by Fast Atom Bombardment Mass Spectrometry in dimethyl sulfoxide (DMSO)/glycerol matrix (Aldrich, Milwaukee, Wis.) on an Ion Tech Mass Spectrometer (Teddington, UK).

Samples were analyzed by proton NMR Spectroscopy in deuterated DMSO (Aldrich, Milwaukee, Wis.) on a Varian XL 301 NMR instrument (Varian, San Fernando, Calif.).

Example 1

Synthesis of a Combinatorial Library Theoretically Containing 136 Different Library Molecules This combinatorial library was generated by reacting the core molecule9,9-dimethylxanthene-2,4,5,7-tetracarboxylic acid chloride with the following derivatized amino acid tool molecules:

H-L-Try-OMe, 60.9 mg;
H-L-Phe-OMe, 51.6 mg;
H-L-Val-OMe, 40.1 mg; and
H-L-Ala-OMe, 33.4 mg The reaction mixture contained 0.239 mmol of each amino acid.

Figure 12:
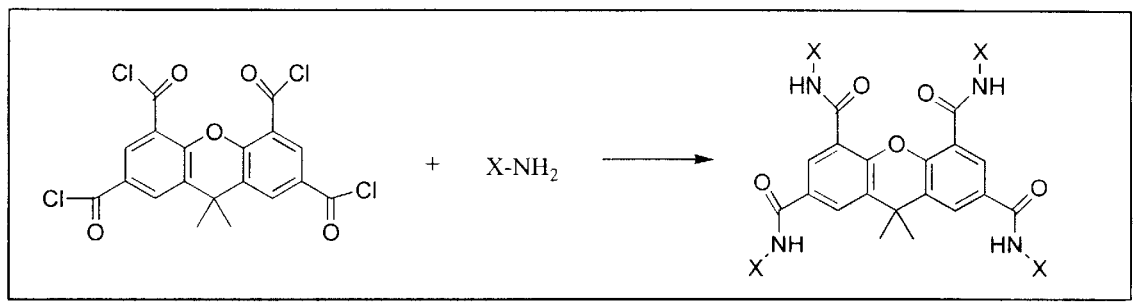
FIG. 12 shows the synthesis and HPLC analysis of a library of 136 theoretical molecules.
Figure 12:
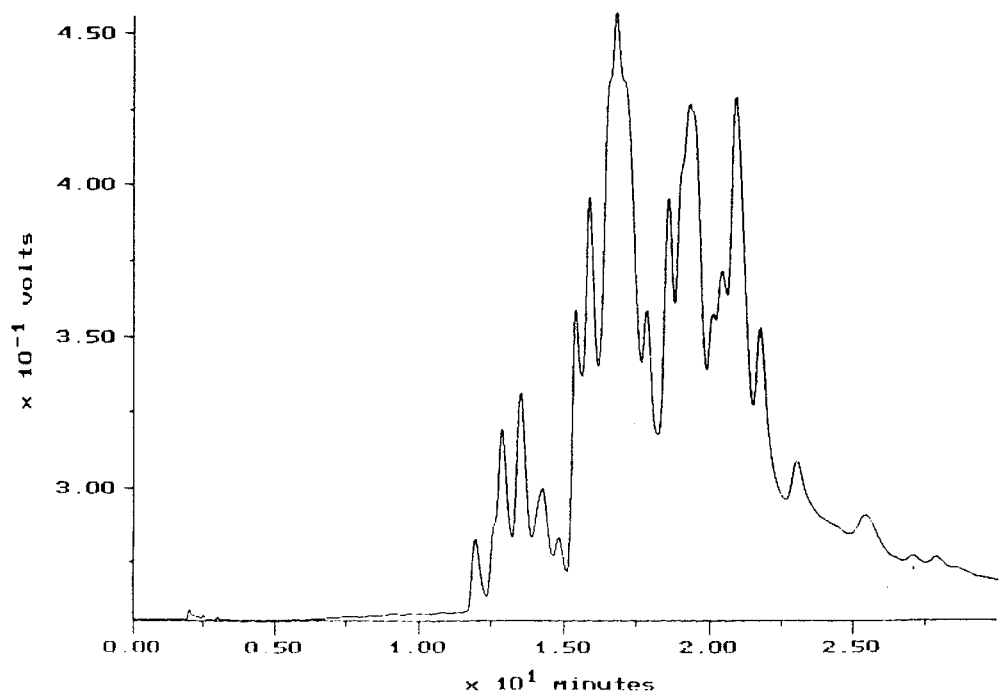

A 10 ml one-neck, round bottomed flask equipped with a magnetic stir bar was charged with xanthene-2,4,5,7-tetracarboxylic acid chloride (100 mg, 0.217 mmol) (synthesized as described in Example 10), the mixture of derivatized amino acid tool molecules (shown above) and 5 ml dichloromethane. The flask was stoppered with a rubber septum containing an argon inlet. One ml of triethylamine was added to the reaction mixture with a syringe and the reaction mixture was stirred under an argon atmosphere for 3 hours. The mixture was diluted with 50 ml of dichloromethane, washed twice with 75 ml of citric acid solution (1M) and washed once with 100 ml of saturated sodium hydrogen carbonate solution. The organic phase was dried over $MgSO_4$ and concentrated to yield a tan oil. The oil was dried under a high vacuum to yield a tan foam. Analytical HPLC analysis of the tan foam is shown in FIG. 12.

Example 2

Synthesis of a Combinatorial Library Theoretically Containing 1225 Different Library Molecules This combinatorial library was generated by reacting the core molecule 9,9-dimethylxanthene-2,4,5,7-tetracarboxyl acid chloride with the following mixture of derivatized amino acid tool molecules:

H-L-Trp-OMe, 34.8 mg H-L-Val-OMe, 22.9 mg H-L-Ala-OMe, 19.1 mg
H-L-Phe-OMe, 29.5 mg H-L-Met-OMe, 27.3 mg H-L-Pro-OMe, 22.6 mg
H-L-Leu-OMe, 24.8 mg

The reaction mixture contained 0.136 mmol of each amine.

Figure 13:
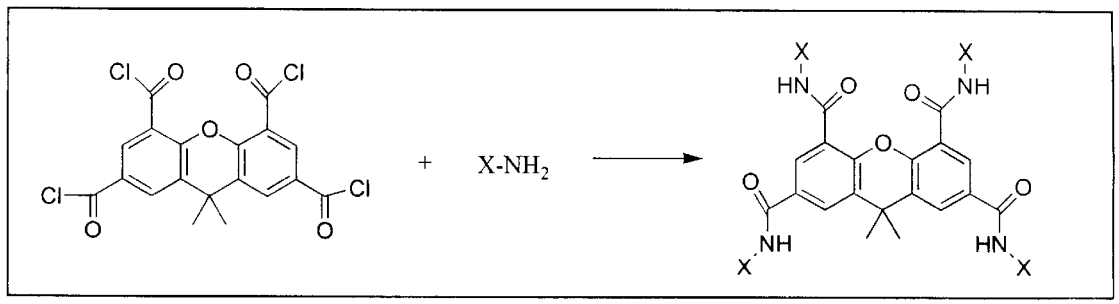
FIG. 13 shows the synthesis and HPLC analysis of a library of 1225 theoretical molecules.
Figure 13:
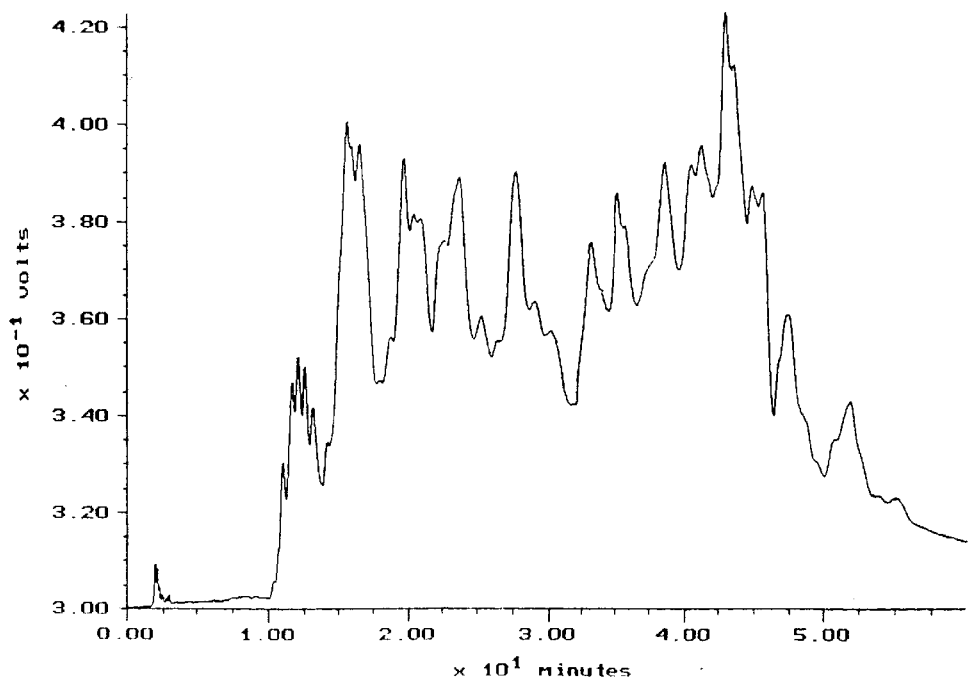

This library was generated using the same procedure as described in Example 1. Analytical HPLC analysis of the tan foam is shown in FIG. 13.

Example 3

Synthesis of a Combinatorial Library Theoretically Containing 10,440 Different Library Molecules This combinatorial library was generated by reacting the core molecule 9,9-dimethylxanthene-2,4,5,7-tetracarboxylic acid chloride with the following mixture of derivatized amino acid tool molecules:

H-L-Ala-OMe, 11.1 mg H-L-Phe-OMe, 17.2 mg H-L-Met-OMe, 15.9 mg
H-L-Pro-OMe, 13.2 mg H-L-Leu-OMe, 14.5 mg H-L-Lys(Boc)-OMe, 23.6 mg
H-L-Ser(tBut)-OMe, 16.9 mg H-L-His(Trt)-$NHR_4$, 34.9 mg
H-L-Asp(OtBut)-OMe, 19.1 mg H-L-Glu(OtBut)-OMe, 20.2 mg
H-L-Thr(tBut)-OMe, 18.0 mg Furfurylamine, 8.4 mg The reaction mixture contained 0.0785 mmol of each amine.

Figure 14:
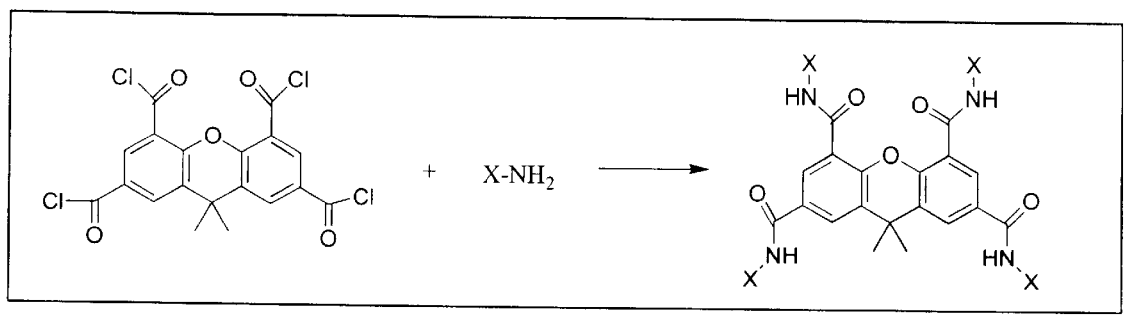
FIG. 14 shows the synthesis and HPLC analysis of a library of 10,440 theoretical molecules.
Figure 14:
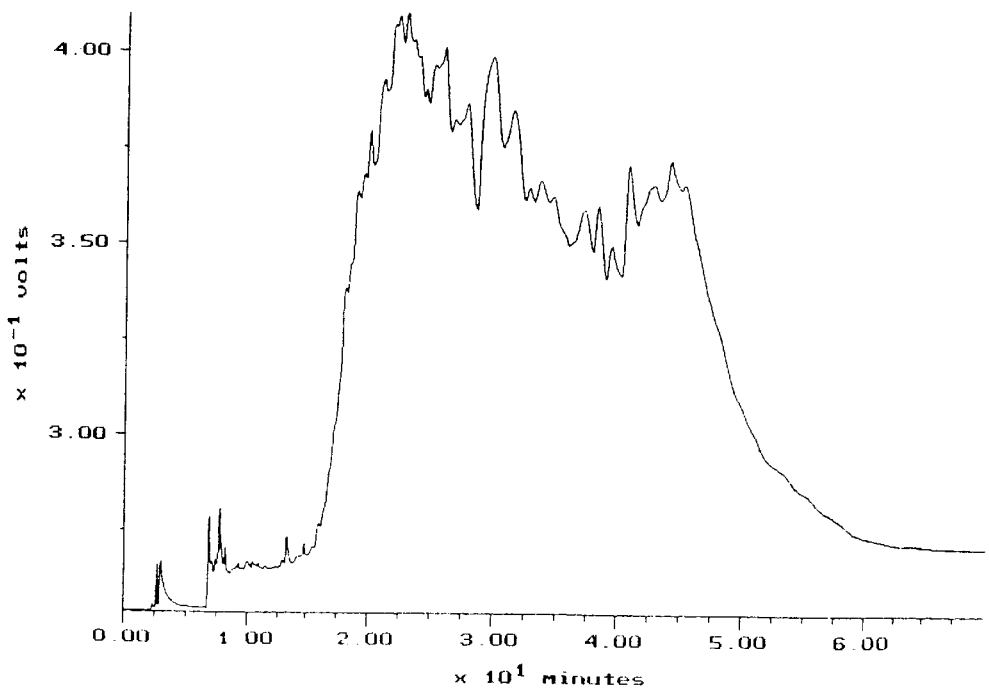

This library was generated using the same procedure as described in Example 1. Analytical HPLC analysis of the tan foam is shown in FIG. 14.

Example 4

Synthesis of a Combinatorial Library Theoretically Containing 97,461 Different Library Molecules This combinatorial library was generated by reacting the core molecule 9,9-dimethylxanthene-2,4,5,7-tetracarboxylic acid chloride with the following mixture of derivatized amino acid tool molecules:

H-L-Trp-OMe, 10.5 mg H-L-Val-OMe, 6.9 mg H-L-Ala-OMe, 5.7 mg
H-L-Phe-OMe, 8.9 mg H-L-Met-OMe 8.3 mg H-L-Pro-OMe, 6.9 mg
H-L-Leu-OMe, 7.5 mg H-L-Lys(Boc)-OMe, 12.3 mg
H-L-Ser(tBut)-OMe, 18.8 mg H-L-His(Trt)-$NHR_4$, 18.1 mg
H-L-Asp(OtBut)-OMe, 9.9 mg H-L-Glu(OtBut)-OMe, 10.5 mg
H-L-Thr(tBut)-OMe, 9.3 mg H-L-Ile-OtBut, 9.3 mg
H-L-Cys(Trt)-$NHR_2$, 18.7 mg H-L-Arg(Mtr)-$NHR_3$, 21.0 mg
H-L-Tyr(tBut)-OMe, 11.9 mg H-L-Val-$NHR_1$, 8.2 mg
4-Methoxybenzylamine, 3.7 mg 1-Methylpyrrol-2-ethylamine, 5.1 mg Furfurylamine, 4.2 mg The reaction mixture contained 0.0413 mmol of each amine.

Figure 15:
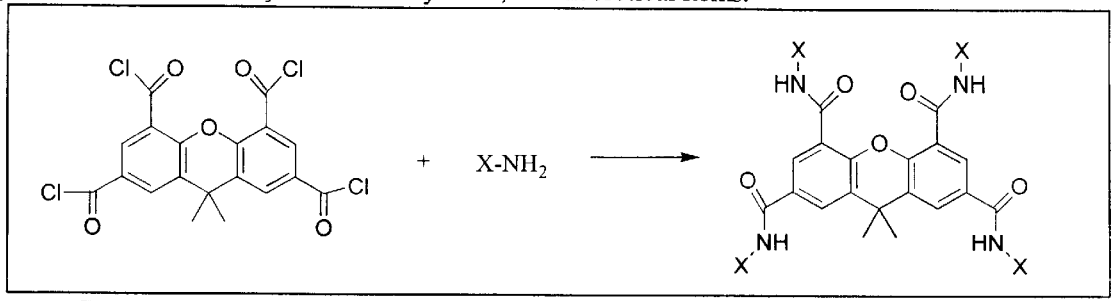
FIG. 15 shows the synthesis and HPLC analysis of a library of 97,461 theoretical molecules.
Figure 15:
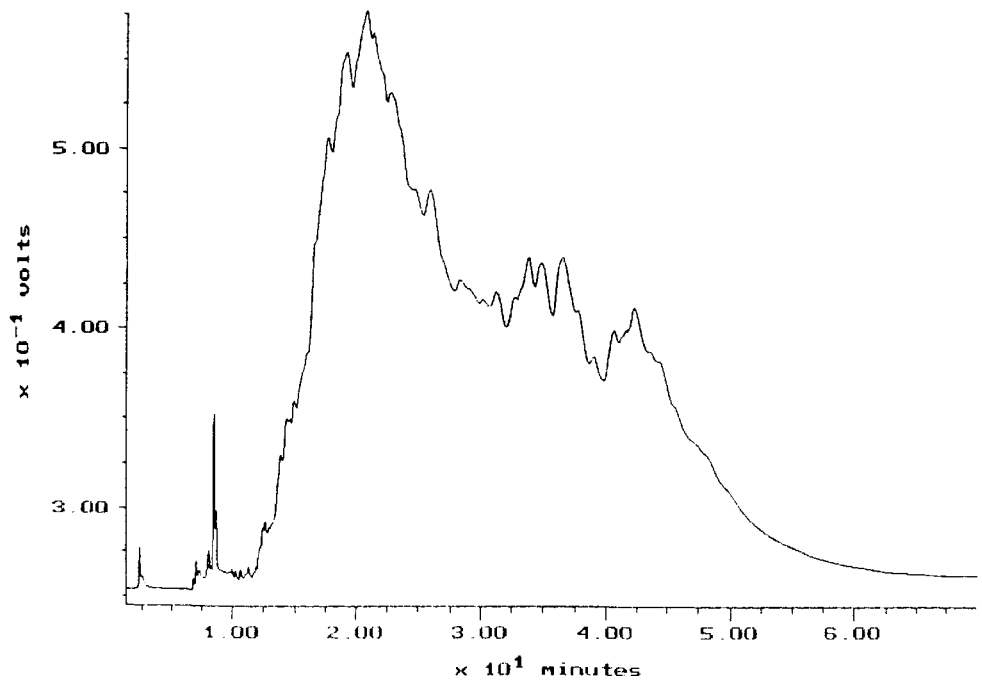

This library was generated using the same procedure as described in Example 1. Analytical HPLC analysis of the tan foam is shown in FIG. 15.

Example 5

Synthesis of a fat-soluble Pro-Library (which can be deprotected to yield a water-soluble Combinatorial Library)

(a) The Synthesis of Amino Acid Tool Molecules containing a Fat-soluble Protecting Group.

Figure 16:
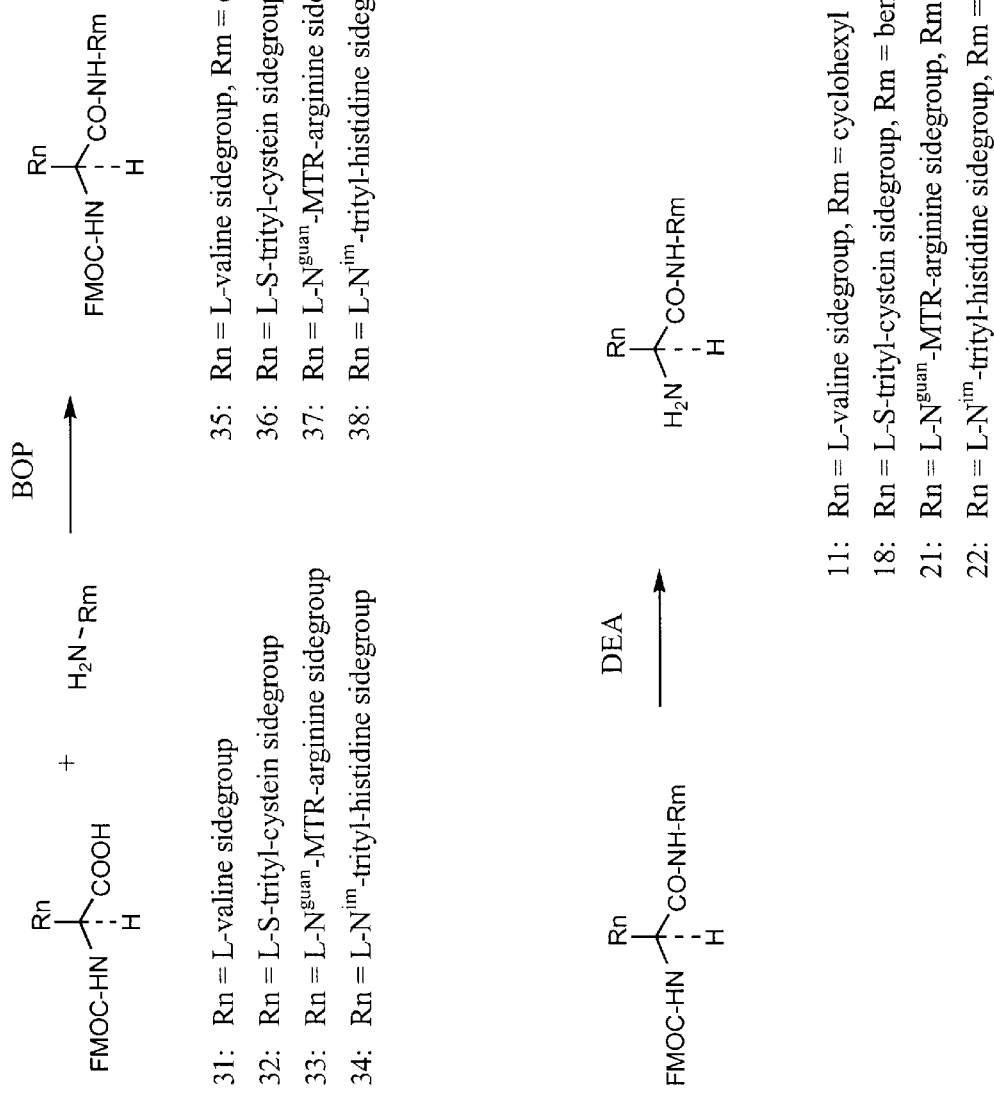
FIG. 16 shows the synthesis of protecting group-derivatized amino acid tool molecules.

Selected amino acid derivatives which were not commercially available were synthesized (e.g., see FIG. 16, compounds 11, 18, 21 and 22). The synthesis of these compounds from the appropriate FMOC-protected amino acid compound (see FIG. 16, compounds 31, 32, 33 and 34) is described below and is illustrated in FIG. 16.

(1) Activation of the FMOC-protected amino acid derivatives and conversion into the amides identified in FIG. 16 as compounds 35, 36, 37 and 38.

The FMOC-protected amino acid derivatives were activated with benzotriazol-1-yloxytris-(dimethylamine) phosphonium hexafluoro-phosphate (BOP) and converted into the amides identified in FIG. 16 as compounds 35, 36, 37 and 38 by reacting with the amines cyclohexylamine, benzylamine, 4-methoxybenzylamine and n-propylamine, respectively (see FIG. 16, the $R_m$—$NH_2$).

A description of the general reaction protocol is provided below, followed by the specific protocols for synthesizing compounds 35, 36, 37 and 38.

General Protocol: A one-neck, round bottomed flask equipped with a rubber septum with an argon inlet and a magnetic stir bar was charged with the FMOC— and side chain-protected amino acid derivative (500 mg), 3 ml of dimethyl formamide and the appropriate amine (recited above). BOP was added and the reaction mixture was stirred at room temperature for 3 hours. The mixture was diluted with 70 ml of dichloromethane, washed twice with 100 ml of citric acid solution (1M) and once with saturated sodium hydrogen carbonate solution. After drying over $MgSO_4$, the mixture was concentrated in vacuo to yield a clear oil. Crude compound 35 (see FIG. 16) was purified by suspending the compound in an appropriate organic solvent (e.g., n-hexane/ethyl acetate (1:1). Compounds 36, 37 and 38 were purified by chromatography on silica gel (described below). The chromatography fractions containing these compounds were concentrated in vacuo to yield a white foam.

Synthesis of Compound 35:

$N^\alpha$-Fluorenylmethoxycarbonyl-L-valine-cyclohexylamide (35) was synthesized by reaction of $N^\alpha$-fluorenylmethoxycarbonyl-L-valine (500 mg, 1.5 mmol) with cyclohexylamine (150 mg, 1.5 mmol) and BOP (680 mg, 1.54 mmol) as the coupling reagent. Isolation of product was achieved by suspending the crude product in n-hexane/ethyl acetate (1:1) and filtration. The residue was collected and concentrated to half of its volume. The slurry thus obtained was again filtered. The combined residues were dried under reduced pressure. The product was obtained as a white solid, 410 mg (66%).

$^1$H NMR (300 MHz,DMSO-d$_6$) δ=7.88 (d,2H,J=7.6 Hz,ar-H), 7.76 (m,3H,ar-H,NH), 7.43 ("t",2H,J=7.3 Hz,ar-H), 7.33 (m,3H,ar-H,NH), 4.22 (m,4H,CH$_2$,α-CH, fluorenyl-H), 3.77 ("t",1H,J=7.0 Hz, (CH$_3$)$_2$—H), 3.50 (br.s, 1H,cyclohexyl-H), 1.90 (m,1H,cyclohexyl-H), 1.70 (br.s, 4H,cyclohexyl-H), 1.55 (br.s,1H,cyclohexyl-H), 1.10–1.35 (m,4H,cyclohexyl-H), 0.85 (s,3H,CH$_3$), 0.82 (s,3H,CH$_3$).

Synthesis of Compound 36:

N-Fluorenylmethoxycarbonyl-S-Trityl-cysteine-benzylamide(36) was synthesized by reaction of N-fluorenylmethoxycarbonyl-S-tritylcysteine (500 mg, 0.85 mmol) with benzylamine (100 mg, 0.93 mmol) and BOP (500 mg, 1.1 mmol) as the coupling reagent. The product was purified by chromatography on silica gel with n-hexane/ethyl acetate (2:1)eluant, R$_f$=0.59. Yield=442 mg (80%).

$^1$H NMR (300 MHz, DMSO-d$_6$) δ=8.45 (br.s, 1H, NH), 7.87 (d, 2H, J=7.6 Hz, ar-H), 7.74 (m, 3H), 7.45–7.08 (m, 24 H), 4.35–4.05 (m, 4H, α-CH, CH$_2$, fluorenyl-H), 2.40 (d, 2H, J=7.3 Hz, CH$_2$-ar).

Synthesis of Compound 37:

$N^\alpha$-Fluorenylrnethoxycarbonyl-Nω-(4-methoxy-2,3,6-trimethyl-benzene-sulfonyl)-arginine-4-methoxybenzylamide (37) was synthesized by reaction of $N^\alpha$-fluorenylmethoxycarbonyl-Nω-(4-methoxy-2,3,6-trimethyl-benzene-sulfonyl)-arginine (550 mg, 0.9 mamol) with 4-methoxybenzylamine (130 mg, 0.95 mmol) and BPO (500 mg, 1.1 mmol) as the coupling reagent. The product was purified by chromatography on silica gel with ethyl acetate as eluant, R$_f$=0.70. Yield=460 mg (70%).

$^1$H NMR (300 MHz, DMSO-d$_6$) δ=8.31 (br.s,1H,NH), 7.94 (s,1H,NH), 7.87 (d,2H,J=7.3 Hz,ar-H), 7.71 (d,2H,J= 7.1 Hz,ar-H), 7.50 (d,1H,J=7.7 Hz,NH), 7.37 ("t",2H,J=7.3 Hz,ar-H), 7.31 ("t",2H,J=7.3 Hz,ar-H), 7.13 (d,2H,J=8.5 Hz,ar-H), 6.82 (d,2H,J=8.3 Hz, ar-H), 6.66 (s,1H,ar-H), 6.40 (br.s,2H,N$^{guan}$-H), 4.20 (m,5H,CH$_2$, fluorenyl-H), 3.98 (m,1H,α-CH), 3.76 (s,3H,OCH$_3$), 3.69 (s,3H,OCH$_3$), 3.03 (m,2H,CH$_2$), 2.87 (s,3H,CH$_3$), 2.72 (s,3H,CH$_3$), 2.03 (s,3H, CH$_3$), 1.70–1.30 (br.s,4H,CH$_2$).

Synthesis of Compound 38:

$N^\alpha$-Fluorenylmethoxycarbonyl-N$^{imid}$-trityl-histidine-prop-1-ylamide (38) was synthesized by reaction of $N^\alpha$-fluorenymethoxycarbonyl-N$^{imid}$-trityl-histidine (500 mg, 0.81 mmol) with n-propylamine (60 mg, 1.0 mmol) and BOP (500 mg, 0.9 mmol) as the coupling reagent. The product was purified by chromatography on silica gel with ethyl acetate as eluant, R$_f$=0.80. Yield=315 mg (59%).

$^1$H NMR (300 MHz, DMSO-d$_6$) δ7.87 (m,3H,ar-H,NH), 7.67 (t,$_1$H,J=7.11 Hz,NH), 7.50–7.20 (m,15H), 7.00 (m,7H), 6.66 (s,1H,his-H), 4.25–4.10 (mn,2H,α-CH,fluorenyl-H), 2.70 (m,2H,CH$_2$), 2.85 (m,2H,CH$_2$), 2.96 (m,2H,CH$_2$), 1.34 (m,2H,CH$_2$), 0.76 (t,3H,J=7.3 HZ,CH$_3$).

(2) Removal of the FMOC-group from compounds 35, 36, 37 and 38 to form the Protecting Group-derivatized amino acid tool molecules identified in FIG. 16 as compounds 11, 18, 21 and 22.

The FMOC-protecting group was removed from compounds 35, 36, 37 and 38 by treatment with diethylamine (DEA) to form the Protecting Group-derivatized amino acids identified in FIG. 16 as compounds 11, 18, 21 and 22. The general reaction protocol is provided below, followed by the structural characteristics for each of compounds 11, 18, 21 and 22.

General Protocol: A 10 ml round bottomed flask equipped with a magnetic stir bar and a septum containing an argon inlet was charged with the FMOC-protected amino acid derivatives 35, 36, 37 or 38; 3 ml of dichloromethane and 3 ml of diethylamine. The reaction mixture was stirred under argon atmosphere at room temperature for 2 hours. The reaction mixture was diluted with 50 ml of dichloromethane and, after the addition of 5 g FLORISIL® (Fisher Scientific Co. Springfield, N.J., a course silica gel), concentrated in vacuo. The product, which precipitated on florisil, was added to the top of a small silica gel column (d=2 cm, 1=15 cm). The column was rinsed with ethyl acetate/n-hexane (1:1) in order to remove the cleaved FMOC.

The free amine (i.e., FMOC-deprotected) product was eluted with methanol/triethylamine (99:1) and was detectable on a kieselgel-precoated TLC plate (Merck & Co., Inc., Rahway, N.J.) by staining with ninhydrin solution. Fractions containing the free amine product were concentrated in vacuo to afford a white foam with a yield greater than 90%.

Compound 11: (L-Valine-cyclohexylamide (11)):

$^1$H NMR (300 MHZ,DMSO-d$_6$) δ7.60 (d,1H,J=7.4 Hz,NH), 3.55 (m,2H, α-CH,cyclohexyl-H), 2.85 (d,1H,J= 5.6 Hz, (CH$_3$)$_2$CH), 1.77–1.60 (br.s,6H,NH$_2$, cyclohexyl-H), 1.60–1.50 (br.s,2H,cyclohexyl-H), 1.45–1.07 (m,4H, cyclohexyl-H), 0.81 (d,3H,J=6.7 Hz,CH$_3$), 0.76 (d,3H,J=6.6 Hz,CH$_3$).

Compound 18: (S-Trityl-L-cystein-benzylamide (18)):

$^1$H NMR (300 MHz,DMSO-d$_6$) δ8.34 (t,1H,J=5.9 Hz,NH), 7.48–7.15 (m,20H, ar-H), 4.35–4.15 (m,2H, CH$_2$Ph), 3.19 (t,1H,J=6.1 Hz,α-CH), 2.39 (dd,1H,J=11.2 and 6.2 Hz, CH$_2$), 2.36 (dd,1H,J=11.7 and 7.3 Hz,CH$_2$), 2.00 (br.s,2H,NH$_2$).

Compound 21: (Nω-(4-Methoxy-2,3,6-trimethyl-benzene-sulfonyl)-L-arginine-4-methoxybenzylamide (21)):

$^1$H NMR (300 MHz, DMSO-d$_6$) δ8.24 (br.s, 1H,NH), 7. 15 (d,2H,J=8.5 Hz,ar-H), 6.85 (d,2H,J=7.3 Hz,ar-H), 6.67 (s, 1H,ar-H), 6.40 (br.s,3H, guanidine-H), 4.18 (d,2H,J=6.2 Hz,CH$_2$), 3.78 (s,3H,OCH$_3$), 3.71 (s,3H,OCH$_3$), 3.12 (br. s, IH,α-CH), 3.00 (m,2H,CH$_2$), 2.59 (s,3H,CH$_3$), 2.51 (s,3H, CH$_3$), 2.35–2.20 (br.s,2H,NH$_2$), 2.04 (s,3H,CH$_3$), 1.60–1.25 (br.s,4H,CH$_2$).

Compound 22: (N$^{imid}$-Trityl-L-histidine-prop-1-ylamide (22)):

$^1$H NMR (300 MHz,DMSO-d$_6$) δ7.79 (t,1H,J=5.8 Hz,NH), 7.40 (m,9H,trityl-H), 7.24 (d,1H,J=1.2 Hz, imid-H), 7.05 (m, 6H, trityl-H), 6.61 (d,1H,J=1.5 Hz, imid-H), 3.33 (m,1H,α-CH), 2.95 (dd,2H,J=13.4 and 7.0 Hz,CH$_2$), 2.73 (dd,1H,J=13.9 and 4.8 Hz,1H,his—CH$_2$), 2.50 (dd,1H, J=14 and 7.2 Hz, his-CH$_2$), 1.93 (br.s,2H,NH$_2$), 1.33 (m,2H, CH$_2$), 0.77 (t,3H,J=7.4 Hz,CH$_3$).

(b) Synthesis of the Pro-Library.

This combinatorial library was generated by reacting the core molecule xanthene-2,4,5,7-tetracarboxylic acid chloride with the following mixture of derivatized amino acid tool molecules:

H-L-Ala-Ot-But, 15.7 mg; H-L-Tyr(t-But)-OH, 20.5 mg;
H-L-Arg(Mtr)-OH, 33.3 mg; H-L-Trp-OMe, 22.0 mg;
H-L-Ser(t-But)-OH, 18.3 mg; H-L-Glu(Ot-But)-Ot-But, 25.5 mg;

H-L-Asn-Ot-But, 19.4 mg; H-L-Val-Ot-But, 18.1 mg; H-L-Asp(Ot-But), 24.3 mg; H-L-Pro-Ot-But, 18.0 mg; H-L-Thr(t-But)-OH, 15.1 mg; H-His(Trt)-OH, 34.3 mg. The reaction mixture contained 0.0865 mmol of each derivatized amino acid tool molecule.

This library was generated using the procedure disclosed in Example 1.

(c) Deprotection of the Pro-Library Molecules.

The above-described foam was dissolved in 3 ml reagent K (82.5% trifluoro acetic acid, 5% phenol, 5% water, 5% thioanisol, 2.5% ethanedithiol (Aldrich, Milwaukee, Wis.) and stirred from 1 to 4 hours (preferably about 2 hours) at room temperature. Reagent K contains a strong acid which is capable of cleaving the protecting groups from the library molecules.

The reaction mixture was concentrated to yield a tan oil which was dried under high vacuum conditions. The dried oil was treated with cold diethylether to extract the cleaved protecting groups, leaving behind a white solid that was collected and dried in vacuo. The white solid (50 mg) is dissolved in water (e.g., 0.5 ml) or a buffered aqueous solution for analysis.

Example 6

Screening procedures using an immobilized ligate

An appropriate amount of the water-soluble combinatorial library is dissolved in a minimum amount of water or buffered solution for performing the screening assay. As used herein, "appropriate amount" refers to an amount which is within the detection limits of the screening assay. In general, the detection limits for an ELISA screening assay are between about 0.1 nM–0.05 mM. Thus, the "appropriate amount" of a library molecule for dissolution will be less for a screening method which employs a more sensitive detection method (e.g., a radiolabeled tag or amplification of the signal prior to detection) and will be more for a screening method which employs a less sensitive detection method.

An affinity matrix containing a plurality of ligate molecules immobilized to an insoluble support (e.g., polyacrylamide, agarose, sepharose) is purchased or synthesized according to methods known to one of ordinary skill in the art. The affinity matrix is washed with buffer prior to applying the combinatorial library molecules. An aliquot of serial dilutions of the combinatorial library (or a fraction thereof, such as a fraction eluted from an HPLC column) is added to the affinity matrix, followed by washing the matrix to remove unbound or non-specifically bound library molecules. The muatrix is contained in a column or is contained in, for example, a microcentrifuge tube for performing a batch separation.

The elution of unbound or non-specifically bound library molecules from the affinity matrix is determined by monitoring, for example, the absorbance at the wavelength at which the library molecules are known to absorb light, or by other detection methods (e.g., thin layer chromatography). Elution fractions containing a detectable amount of library molecules are collected, concentrated and analyzed. Optionally, the affinity matrix is rinsed with a concentrated solution of a ligand that is known to bind to a specific region of the ligate. Accordingly, washing the matrix with a solution of the ligand specifically elutes compounds that bind to the same region of ligate. The eluted fractionns) are subjected to the analysis procedure (described below). Alternatively, or additionally, the affinity matrix is rinsed with a solution of a denaturant which denatures the immobilized ligate, thereby releasing library molecules which have specifically bound to the immobilized ligate. The eluted fractions) then are subjected to the analysis procedure. The following example is intended to illustrate the above-disclosed general process for using an immobilized ligate to identify lead compounds in a combinatorial library. The example is not intended to limit the invention to a particular embodiment.

The carbohydrate-binding protein concanavalin A (Con A) covalently bound to sepharose is purchased (e.g., Sigma Chemical Co., St. Louis, Mo.). An appropriate amount of the library molecules are added to 20 ul of Con A-Sepharose contained in a microcentifuge tube, in a final volume of 200 ul Con A Buffer (50 mM NaCl/20 mN Mops, pH 6.8/2 mM $MgCl_2$/2 mM $CaCl_2$/0.2 mM EDTA). (See, e.g., Oldenburg, K., et al., Proc. Nat. Acad. Sci. USA 89:5393–5397 (1992)). The library molecules are allowed to bind to the Con A-Sepharose for 1–24 hours at room temperature with agitation. Unbound or non-specifically bound library molecules are removed by washing the Con A-Sepharose with Con A Buffer (e.g., three 5 minute washes) (described above). Specifically-bound library molecules are eluted with either 200 mM methyl alpha-D-mannopyranoside, 1% mannan, or 100 mM citrate buffer (pH 3.0) for at least about 30 minutes at room temperature and are subjected to the analysis procedure (described below).

Example 7

Screening procedures using a soluble ligate

Combinatorial library molecules are assayed in a competition ELISA format over a concentration range of about 0.1 nM–0.05 mM for each library molecule using procedures familiar to the artisan of ordinary skill in the art (see, e.g., Zuckermann, R., et al., Proc. Nat. Acad. Sci. USA 89:4505–4509 (1992). Microtiter plates are coated (e.g., about 0.2 ug ligand per well in 50 mM borate, pH 9.0, overnight at 4° C.) with a known ligand of the antibody ligate for which lead compounds are being screened. To the ligand-coated microtiter wells is added a 50 ul aliquot of serial dilutions of the combinatorial library (or a fraction thereof, such as a fraction eluted from an HPLC column) with 50 ul of a diluted ligate antibody solution that is known to give a positive, detectable ELISA signal when incubated with the ligand-coated microtiter well in the absence of a soluble competitor of the immobilized ligand. Wells to which no combinatorial library molecules are added are included as assay controls. Typically, the incubations are performed in a Tris-buffer for about one hour at 37° C. The microtiter plates are washed to remove unbound or non-specifically bound antibody ligate, followed by incubating with a detection reagent (e.g., 100 ul of horseradish peroxidase-conjugated goat anti-mouse antibody (stock solution of 1 mg/ml diluted 1:1000, Boehringer Mannheim)) for about one hour at 37° C. and washed as above to remove unbound or non-specifically bound conjugated antibody. The amount of bound conjugated antibody is quantitated by color development with 100 ul of o-phenylenediamine at 5 mg/ml in 50 mM sodium citrate/0.02% $H_2O_2$, pH 5.1 and measurement of the absorbance at 450 nm. The presence of a library molecule which specifically inhibits the binding of the antibody ligate to its known (immobilized) ligand is indicated by a reduction in the absorbance at 450 nm. The library molecules which specifically inhibit the binding are subjected to the analysis procedure described below.

Example 8

Iterative Screening Procedure

An exemplary iterative screening procedure that has been used to identify two different trypsin inhibitors is provided in Example 11. The exemplary procedure follows the strategy outlined below.

A known number of tool molecules (X) are used to generate a first combinatorial library. The library is screened to identify library molecules which modulate the biological activity of an immobilized ligate (see, e.g., Example 6) or a soluble ligate (see, e.g., Example 7). For example, the ability of a library molecule to modulate the biological activity of an enzyme is determined by observing a change in enzyme activity as increasing amounts of library molecules are included in the enzyme assay reaction mixture. Thus, a number of different screening assays can be used to quantitate the effect of the first combinatorial library on the biological activity of the ligate.

A second combinatorial library is prepared using the same mixture of tool molecules as used to generate the first combinatorial library with one exception: one of the tool molecules included in the generation of the first library is absent from the mixture of tool molecules used to generate the second library. By comparing the effect of the first and second libraries on the biological activity of the ligate, one can determine whether the omitted tool molecule is necessary or unnecessary for ligate binding. Moreover, by applying this iterative procedure to each of the tool molecules used to generate the first combinatorial library, the identity of each tool molecule that is involved in binding to the ligate is determined.

Example 9

Analysis Procedure

A fraction containing the library molecules of interest (e.g., a fraction which has exhibited binding to an immobilized ligate) is subjected to mass spectroscopy and the empirically obtained mass values are compared to the theoretical mass values calculated for each possible compound in the combinatorial library. By matching the empirically obtained mass values and calculated mass values, the molecular weights of library molecules that are able to bind to the ligate are deduced.

Ideally, the structures of the library molecules of interest are deduced from their molecular weights. However, if the structure of a library molecule is not uniquely determined by its molecular weight, an iterative process is used to identify the structure of the biologically active library molecule. The iterative process involves generating a second combinatorial library using only those tool molecules having molecular weights which the mass spectroscopy data indicates are present in the biologically active fraction. As a result, the second library contains a higher concentration of the biologically-relevant library molecules, a factor which facilitates mass spectroscopy analysis.

The second library is screened, subjected to mass spectroscopy and the empirical mass values are compared to the theoretic mass values (as described above) to deduce the structures of the library molecules of interest. This process is repeated until there is sufficient molecular weight data to determine the structure of the biologically active library molecule.

Example 10

Synthesis of 9,9-dimethylxanthene diacyl- and tetraacyl- chloride

Figure 17:
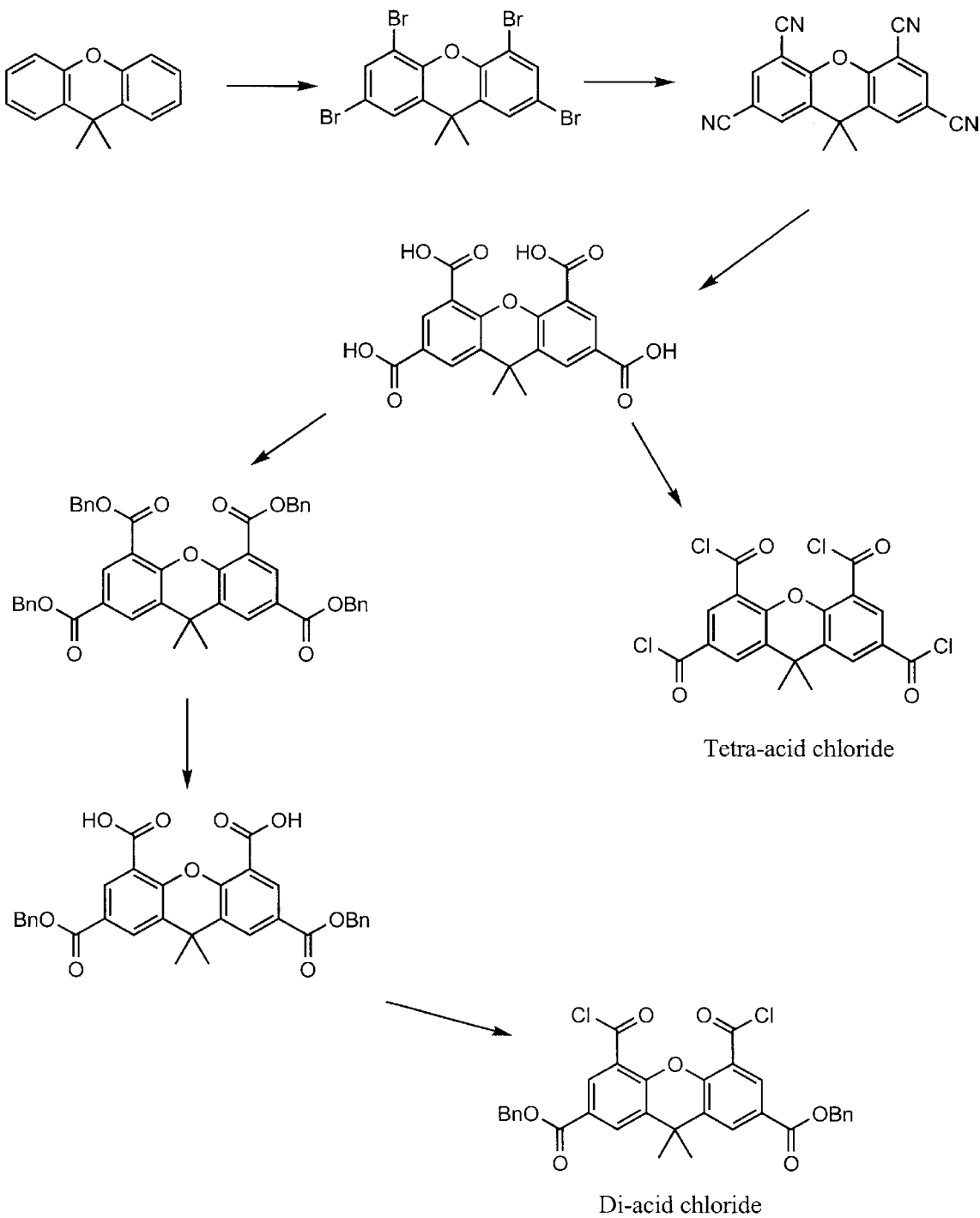
FIG. 17 shows the synthesis of 9,9-dimethylxanthene 2,4,5,7-di- and tetra-acid chloride core molecules.

FIG. 17 schematically illustrates this synthesis procedure.
Synthesis of 9,9-Dimethylxanthene-2,4,5,7-tetrabromide:

A 50-mL, one-necked, recovery flask fitted with an addition funnel and magnetic stirring bar was charged with $Br_2$ (14.971 g, 93.674 mmol) and 25 mL of $CH_2$—$Cl_2$ and cooled in an ice bath. 9,9Dimethylxanthene (4.924 g, 23.42 mmol) was added over 10 min. After 45 min, Fe powder (0,030 g, 0.54 mmol) was added, and the reaction mixture was allowed to warm to room temperature over 2.5 h. The recovery flask was fitted with a condenser attached to a mineral oil bubbler, and the reaction mixture was heated at reflux until the condensate became colorless (2.5 h). The resulting solution was extracted with 30 mL of $H_2O$, dried over $MgSO_4$, filtered, and concentrated to afford a white solid. The solid was boiled with 30 mL of ethanol, and the resulting suspension allowed to cool to room temperature. Filtration, followed by drying in vacuo afforded 11.477 (93%) of 4 as a white solid: mp 152°–154° C; $^1$H NMR ($CDCl_3$, 5090 MHz) $\delta$7.64 (d,J=2.0 Hz,2H), 7.44 (d,J=2.5 Hz,2H), 1.60 (s,6H); HRMS m/e calculated for $C_{15}H_{10}^{79}Br_4O$: 521,7476, found 521.7465.

Synthesis of 9,9-Dimethylxanthene-2,4,5,7-tetranitrile:

Copper cyanide (25.89 t, 4.4 eq) was weighed out in a flask fitted with a reflux condensor and drying tube. Methyl-2-pyrrolidione (100 mL) and tetrabromo dimethylxanthene (34.6 g, 1 eq) were added, and the mixture was refluxed for 2 h.

The olive green reaction mixture was filtered. The solid washed well with water and added to 250 mL of 20% nitric acid, evolving red gas ($NO_2$) vigorously. The brilliant green mixture was stirred overnight, then filtered to yield a beige solid (20.36 g, 99.6% yield.)

$^1$H NMR ($CDCL_3$) $\delta$8.55 (d,J=1.9 Hz,2H), 8.47 (d,J=1.9 Hz,2H), 1.66 (s,6H).

Synthesis of 9,9-Dimethylxanthene 2,4,5,7-tetraacid:

The xanthene tetranitrile (5.00 g, 1 eq) was suspended in $H_2O$ (20 mL). Sodium hydroxide (3.21 g) in 20 mL water was added, and the brown mixture was stirred at ref lux for 14 h.

The clear brown solution was acidified, with 2.0M HCl, precipitating the product. The aqueous layer was repeatedly extracted with THF/EtOAc(1:1) until clear. The combined organic portions were dried over $Na_2SO_4$ and stripped, giving a beige solid (6.127 g, 98.8% yield).

$^1$H NMR (DMSO) $\delta$13.19 (s broad, 4H), 8.25 (d,J=2.0 Hz,2H), 8.15 (d,J=2.0 Hz,2H), 1.66 (s,6H).

Synthesis of 9,9-Dimethylxanthene-2,4,5,7-tetracarboxylic acid chloride:

A 250 mL one-necked round bottomed flask fitted with a magnetic stir bar and a reflux condenser was charged with phosphoropentachloride (7 g, 0.03 mol), 9,9-dimethylxanthene-2,4,5,7-tetracarboxylic acid (3 g, 7.8 mmol) and 100 mL of benzene. The reaction mixture was refluxed for 12 h and concentrated to a final volume of 25 mL. The mixture was kept at 4° C. overnight. The acid chloride precipitate was filtered off and washed three times with 3 mL of benzene. The product was obtained in the form of small brownish platelets. Yield=2.3 g (65%).

$^1$H NMR (300 MHz, DMSO-$d_6$) $\delta$8.25 (d,2H,J=2.0 Hz,ar-H), 8.15 (d,2H,J=2.0 Hz,ar-H), 1.68 (s,6H,$CH_3$): MS (E1) m/z (%)=460 (3) [M+], 445 (100) [M+—$CH_3$], 423 (54), 380 (31), 317 (18), 254 (11), 194 (16), 163 (21).

Synthesis of 9,9-Dimethylxanthene-2,4,5,7-tetrabenzyl ester:

5.43 g (14.056 mmol) 9,9-Dimethylxanthene 2,4,5,7-tetra acid chloride was stirred with 10 ml (excess) benzyl alcohol and 10 ml pyridine in 100 ml $CH_2Cl_2$. The dark brown solution was stirred overnight and then extracted with 200 ml 1.0N HCl and 200 ml brine. The organic layer was dried over MgSO$_4$ and poured into 100 ml methanol (MeOH). The precipitate was broken up and stirred in solution for one hour, after which it was filtered off and washed with MeOH. The product was an off-white colored solid, 6.98 g, 67% yield.

Synthesis of 9,9-Dimethylxanthene-2,7-dibenzyl-4,5-dicarboxylic acid:

3.0 g 9,9-Dimethylxanthene-2,4,5,7-tetrabenzyl ester were dissolved in 100 ml dry CH$_2$Cl$_2$. HBr was bubbled through the stirring solution for 15 minutes, and the solution was stoppered and allowed to stir 24 hours. The cloudy solution was quenched with 100 ml H$_2$O and shaken well. 100 ml tetrahydrofuran (THF) were added, and the solution was extracted with 3×200 ml H$_2$O and 100 ml brine. The organic layer was dried over MgSO$_4$ and rotoevaporated to a light yellow solid. Recrystalization from THF, Hexanes yielded 2.0 g product, 90%.

Synthesis of 9,9-Dimethylxanthene-2,7-dibenzyl-4,5-diacidchloride:

60 mg (0.11 mmol) 9,9-Dimethylxanthene-2,7-dibenzyl-4,5-dicarboxylic acid were suspended in 1 ml CH$_2$cl$_2$ and 0.5 ml Oxalyl chloride. The reaction flask was fitted with a condenser, 3 drops Dimethylformamide were added, and the solution was refluxed for 2 hrs. The solution was diluted with 10 ml CH$_2$Cl$_2$ and stripped to a yellow-white solid. The yield was 55 mg product, 91%.

Example 11

Figure 18:
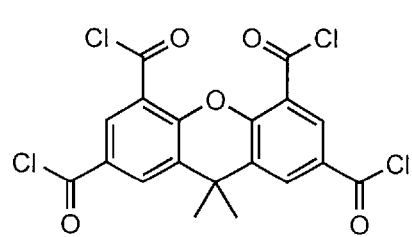
FIG. 18 shows the two tetraacid chloride core molecules 1 (xanthene tetraacid chloride) and 2 (cubane tetraacid chloride)
Figure 18:
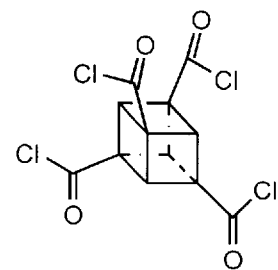

A Solution Phase Screening Procedure for the Isolation of Active Compounds from a Molecular Library Introduction:

The foregoing Examples describe an approach to molecular diversity that produces structurally biased libraries of small molecules. Because the new process for creating libraries of molecular diversity uses neither coding schemes nor spatially isolated molecules, conventional methods for screening and amplification are not applicable. Accordingly, a solution phase selection-amplification procedure for use with the libraries is described herein. Library Construction: All of the libraries were constructed by following a two-step procedure. In the first step, a core molecule, such as cubane tetraacid chloride 2 or xanthene tetraacid chloride (130.2 mg) 1 (FIG. 18), was dissolved in 4 ml dichloromethane and condensed with the following 19 derivatized (commercially available) amino acid tool molecules:

List of the tool molecules, abbreviations and amount used:
Tool Molecules that were used as the HCL salt:
L-alanine-tert-butyl ester (Ala), 10.8 mg;
L-asparagine-tert-butyl ester (Asn), 13.4 mg;
L-aspartic acid-beta-tert-butyl-alpha-tert- butyl ester (Asp), 16.8 mg;
L-glutamic acid-gamma-tert-butyl-alpha-tert-butyl ester (Glu), 17.6 mg;
Glycine-methyl ester (Gly), 7.5 mg;
L-isoleucine-tert-butyl ester (Ile), 13.3 mg;
L-leucine-tert-butyl ester (Leu), 13.3 mg;
N-epsilon-Boc-L-lysine-methyl ester (Lys), 17.7 mg;
L-methionine-methyl ester (Met), 11.9 mg;
L-phenylalanine-tert-butyl ester (Phe), 15.3 mg;
L-proline-tert-butyl ester (Pro), 12.4 mg;
O-tert-butyl-L-serine-tert-butyl ester (Ser), 15.1 mg;
O-tert-butyl-L-threonine-methyl ester (Thr), 13.4 mg;
L-tryptophane-methyl ester (Trp), 15.2 mg;
O-tert-butyl-L-tyrosine-methyl ester (Tyr), 17.1 mg;
L-valine-tert-butyl ester (Val), 12.5 mg.
Tool molecules that were used as the free amine:
N$^g$-4-methoxy-2,3,6-trimethylbenzene -sulfonyl-L-arginine (Arg), 23.0 mg;
N$^{im}$-trityl-L-histidine (His), 23.7 mg;
S-trityl-L-cysteine (Cys), 21.6 mg.

As described above, the diversity obtained by this reaction is determined by the number of tool molecules used and by the symmetry of the core molecule. With the 19 tool molecules and the xanthene core molecule 1 (FIG. 18), 65,341 different variants were theoretically produced. By using the cubane core molecule 2 with its higher symmetry, only 11,191 possible compounds could be generated from the same set of tool molecules. In the second step, the generated libraries were treated with a trifluoroacetic acid based reagent (Reagent K, described above) to remove acid-labile protection groups present on certain tool molecules. After precipitation with diethyl ether and n-hexane, the mixtures were obtained in the form of white powders with sufficient solubility in a 9:1 mixture of water/dimethylsulfoxide for further enzymatic studies.

Trypsin Inhibitor Assay.

The rate of the trypsin catalyzed reaction was determined by monitoring the increase in absorbance at 410 nm over time. In all measurements 5% (v/v) of dimethylsulfoxide (DMSO) was added to solubilize the libraries. For a typical assay, 50 μL of a library solution in DMSO and 10 μL of the trypsin stock solution (2.5 mg trypsin in 25 mL 0.001M HCl) were added to 5 mL of buffer (0.5M Tris-HCl, 0.16M CaCl$_{21}$ pH 8.2) at 25° C. In regard to FIG. 19, the library solutions used for Charts A and B contained 2.5 mg in 50 μL DMSO; the library solution for Chart C contained 1 mg in 50 AL DMSO and the library solution for Chart D contained 0.5 mg in 50 μL DMSO.

After incubating for 10 min., the cloudy mixture was centrifuged, 0.4 mL of the clear supernatant was removed and diluted with 400 μL of buffer in a disposable 1.5 mL UV cuvette. Then, 50 μL of the BAPA (defined below) stock solution (50 mg BAPA in 5 mL DMSO) was added and the increase in absorbance at 410 nm was monitored. The trypsin activity was compared to a reference cuvette without added library material (B).

Iterative Screening Procedure.

The screening procedure used the above-noted trypsin assay which was based upon a published protocol (B. F. Erlanger, et al., Arch. Biochem. Biophys. 95:271–278 (1961); H. F. Gaertner, et al., Enzyme Microb. Technol. 14:150–155 (1992). (See also J. Eichler, et al., Biochemistry 32:11035–11041 (1993)). The objective of the screening procedure was to identify a compound within the library which inhibited the trypsin-catalyzed hydrolysis of the amide bond in Nα-benzoyl-L-arginine-p-nitroanilide (BAPA). Accordingly, the amount of trypsin inhibitor activity present the library aliquot tested in the trypsin assay was inversely proportional to the rate of p-nitroaniline released by trypsin in the assay.

Figure 19:
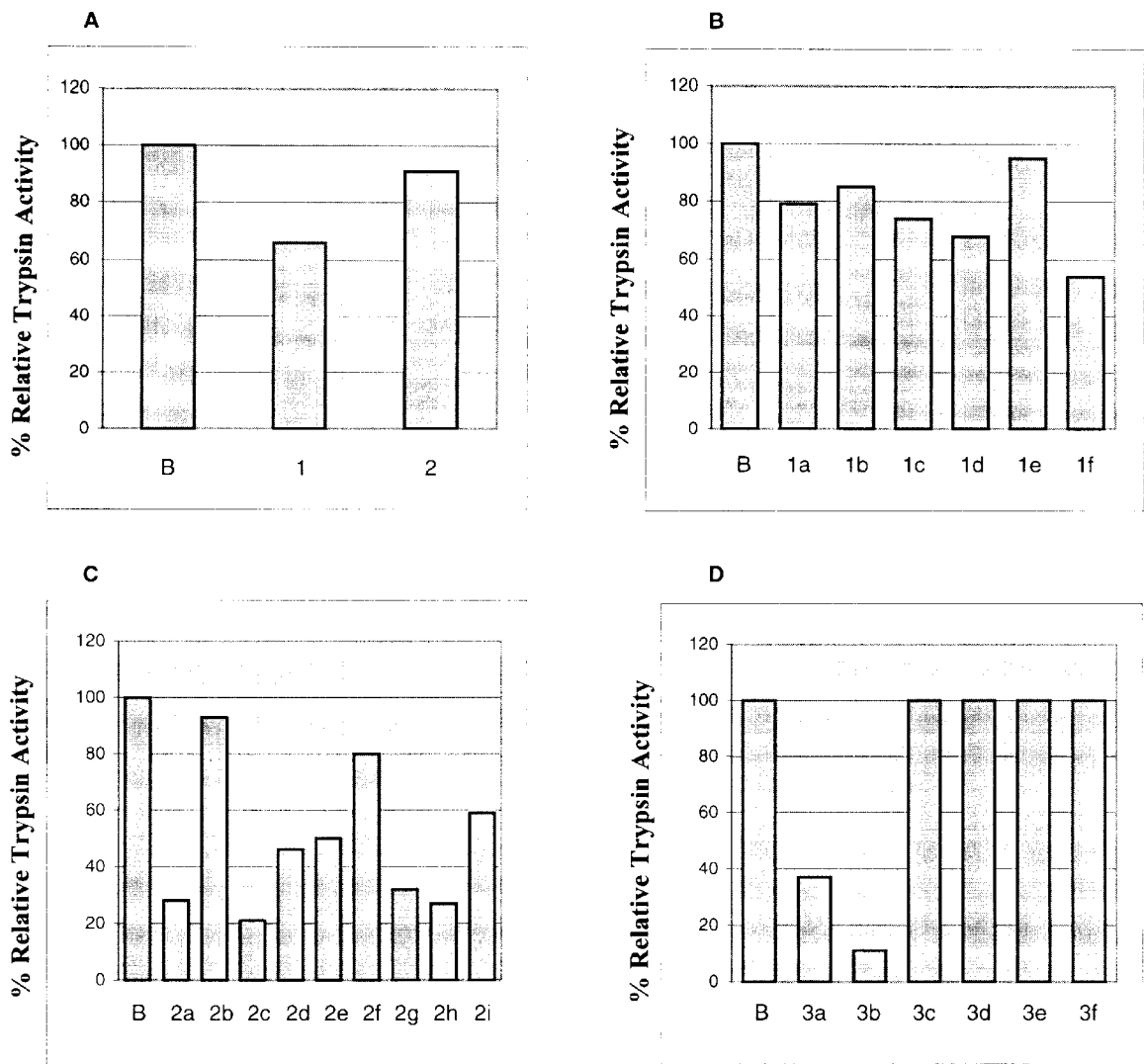
FIG. 19 shows the iterative screening procedure results for identifying a trypsin inhibitor in the molecular libraries; Chart A depicts % trypsin activity in the initial libraries 1 and 2 constructed from the libraries generated with core molecules 1 or 2 and 19 tool molecules; Chart B depicts % trypsin activity of the six sub-libraries 1A–1F generated with core molecule 1 and 15 of the 19 tool molecules; Chart C depicts % trypsin activity in the nine sub-libraries 2A–2I, each synthesized with core molecule 1 and 8 different tool molecules; and Chart D depicts % trypsin activity in the sub-libraries 3A–3F (see Table 3 for a description of their composition)

FIG. 19, Chart A depicts the screening results obtained from the initial libraries 1 and 2 generated by reacting core molecules 1 and 2 (FIG. 18), respectively, with the above-identified 19 amino acid derivative tool molecules. Even though both libraries were constructed using the same set of tool molecules, only library 1 caused a significant reduction of trypsin activity (approximately 30%). The fact that the library 2, based on the cubane core molecule 2, did not substantially interfere with the enzyme reaction (activity 91%) suggested that the presence of certain functional groups alone is not sufficient to produce a trypsin inhibitor. Thus, other factors, including the spatial orientation of the tool molecules with respect to one other and the core molecule, also are important.

In order to determine which of the 19 tool molecules were essential for generating an active library, two further screening procedures were carried out (FIG. 19, Charts B and C). In the first experiment (designed to reduce the number of potentially active tool molecules from 19 to about nine), the tool molecules (without cysteine) were divided into six groups, GA-GF, identified in Table 3.

TABLE 3

List of three tool molecules in each of the six groups GA-GF

| GA | GB | GC | GD | GE | GF |
|---|---|---|---|---|---|
| Gly | Leu | Phe | Ser | Arg | Glu |
| Ala | Ile | Tyr | Thr | Lys | Asp |
| Val | Pro | Trp | Met | His | Asn |

Six different sub-libraries 1A–1F were synthesized using the xanthene core molecule 1 and only five of the six tool molecule groups. To illustrate, Group GA was omitted during synthesis of sub-library 1A; Group GB was omitted during synthesis of sub-library 1B; Group GC was omitted during synthesis of sub-library 1C; Group GD was omitted during synthesis of sub-library 1D; Group GE was omitted during synthesis of sub-library 1E; and Group GF was omitted during synthesis of sub-library 1F. Each sub-library 1A–1F was tested for its ability to inhibit trypsin activity and the percent trypsin activity was correlated to the specific tool molecule group (see Table 3) that had been omitted during synthesis of the sub-library being assayed.

The results (FIG. 19, Chart B) were used to rank the tool molecule groups in order of inhibitor activity. The sub-libraries 1A, 1B and 1E (synthesized by omitting the amino acid derivative tool molecules in groups GA, GB and GE) exhibited the greatest trypsin activity. Accordingly, groups GA, GB and GE contained the nine amino acid derivatives with highest trypsin inhibitor activity in the context of the xanthene skeleton. These nine tool molecules were selected for further activity study.

The next screening step further reduced the number of possibilities for the most important amino acid derivatives among the nine tool molecules in Groups GA, GB and GE. Because each screening step substantially reduced the number of tool molecules used to synthesize the subsequent set of sub-libraries, the subsequent sets of sub-libraries produced during the screening process were considerably less complex. Moreover, sequential reduction in the number of tool molecules used to generate subsequent sub-libraries resulted in an "amplification" effect, i.e., the amount of trypsin inhibitor activity in the later sub-libraries was observed to increase due to an increase in the proportional amount of the active inhibitor(s) present in the sub-libraries.

Nine sub-libraries (2A–2I) were synthesized with sequential omission of one specific amino acid derivative. Thus, amino acid derivative tool molecules Arg, Lys, His, Leu, Ile Pro, Gly, Ala, and Val were omitted during the reaction of the xanthene core molecule 1 to form sub-libraries 2A, 2B, 2C, 2D, 2E, 2F, 2G, 2H and 2I, respectively. The screening results obtained for these nine sub-libraries are presented in FIG. 19, Chart C.

The results indicate that the sub-libraries 2B, 2D, 2E, 2F and 2I (created without the tool molecules Lys, Leu, Ile, Pro and Val, respectively) exhibited very high anti-trypsin activities. These tool molecules were therefore deduced to be predominantly responsible for the generation of the trypsin inhibitor(s).

Further sub-libraries, generated from the xanthene core molecule 1 and mixtures of three or four of the five tool molecules Lys, Pro, Val, Ile, and Leu, confirmed that a library constructed using the four amino acid derivatives, Lys, Pro, Val and Ile possessed the highest anti-trypsin activity. Omission of one of these four tool molecules gave libraries with significantly reduced inhibitory activity.

Figure 20:
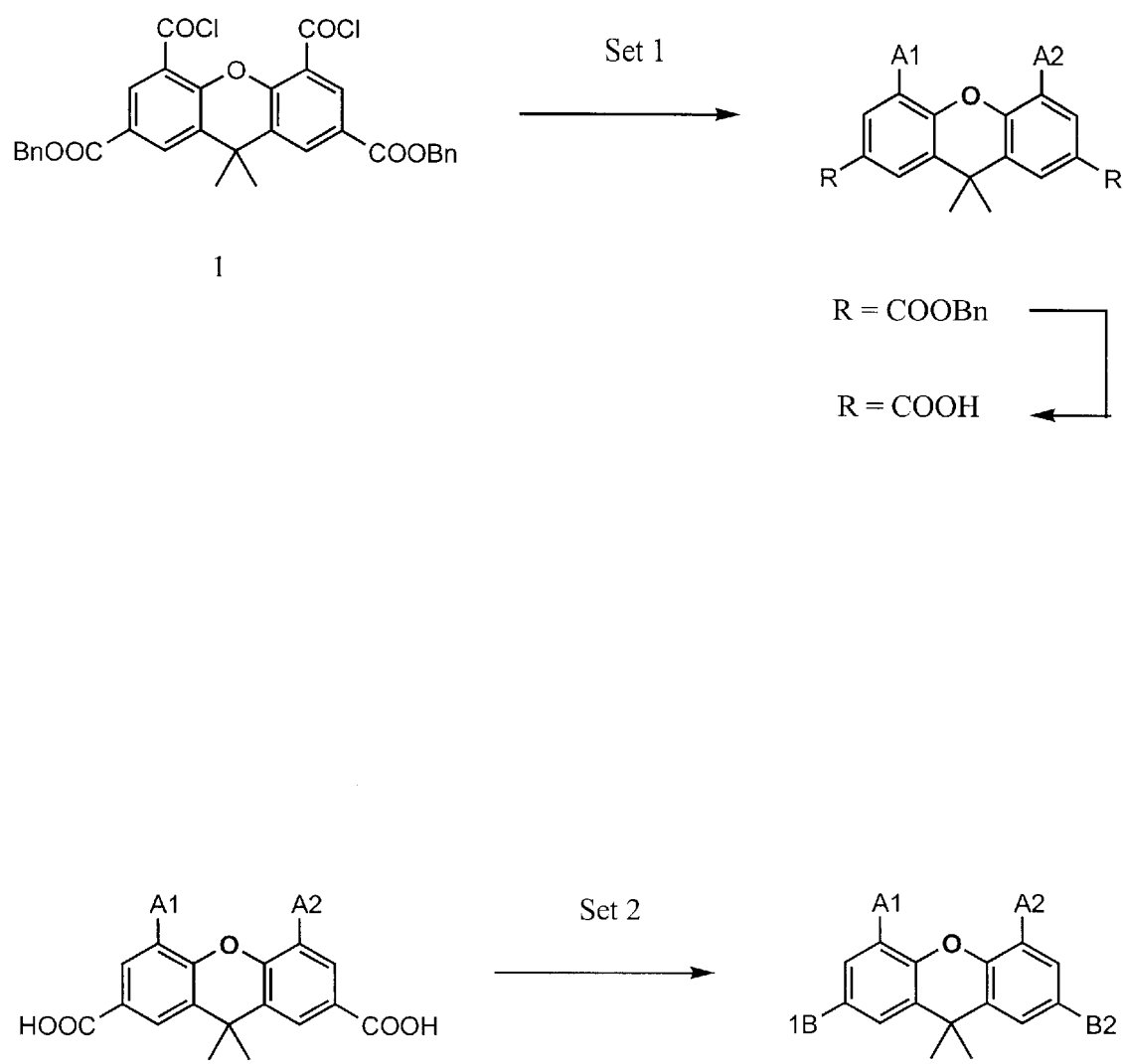
FIG. 20 shows a schematic representation of the synthesis of six sub-libraries (3A–3F) designed to determine the orientation of the tool molecules Lys, Val, Ile and Pro around the xanthene core molecule skeleton. A1 and A2 represent the building blocks of Set 1, B1 and B2 represent the building blocks of Set 2 (see also Table 4)

To determine the orientation of the tool molecules Lys, Val, Ile and Pro around the xanthene core molecule skeleton of the most potent trypsin inhibitor, six additional sub-libraries (3A–3F) were generated following the synthetic procedure outlined schematically in FIG. 20. In this figure, A1 and A2 represent the tool molecules of Set 1, B1 and B2 represent the tool molecules of Set 2 (see Table 4).

TABLE 4

List of the tool molecules used as Set 1 (A1, A2) and Set 2 (B1, B2)

| Library | Set 1 ($A_1$, $A_2$) | Set 2 ($B_1$, $B_2$) |
|---|---|---|
| 3A | Lys, Val | Ile, Pro |
| 3B | Lys, Ile | Val, Pro |
| 3C | Lys, Pro | Ile, Val |
| 3D | Val, Ile | Lys, Pro |
| 3E | Val, Pro | Lys, Ile |
| 3F | Ile, Pro | Lys, Val |

For each sub-library, the dibenzyl ester protected xanthene diacid chloride (FIG. 20, compound #3) was first reacted with only two of the four tool molecules (Table 4, Set 1). Debenzylation by hydrogenation of the resulting three compound mixture ($H_2$; Pd/C, 10%; 9:1 mixture of ethyl acetate/ethanol) followed by reaction with the other two tool molecules (Table 4, Set 2; BOP; DMF; TEA) yielded a mixture containing twelve compounds. After cleavage of the acid-labile protection groups, six new sub-libraries 3A–3F were obtained, each with a unique distribution of the four building blocks around the xanthene skeleton. Table 4 contains a list of the amino acid derivatives used as the first (Set 1) and the second (Set 2) set of tool molecules for the synthesis of the six sub-libraries (3A–3F).

Figure 21:
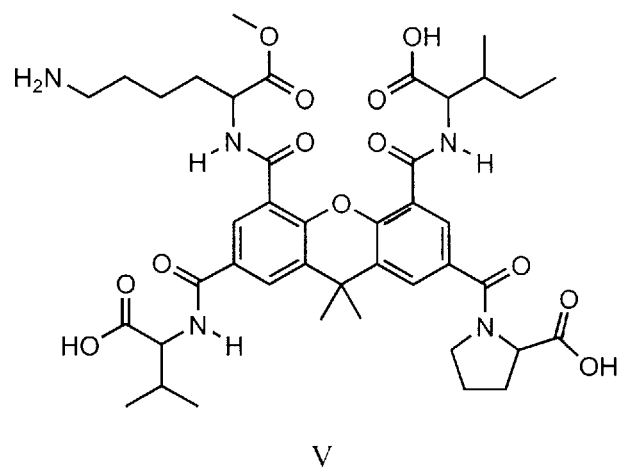
FIG. 21 shows the structure of trypsin inhibitors of Formula V and Formula VI.
Figure 21:
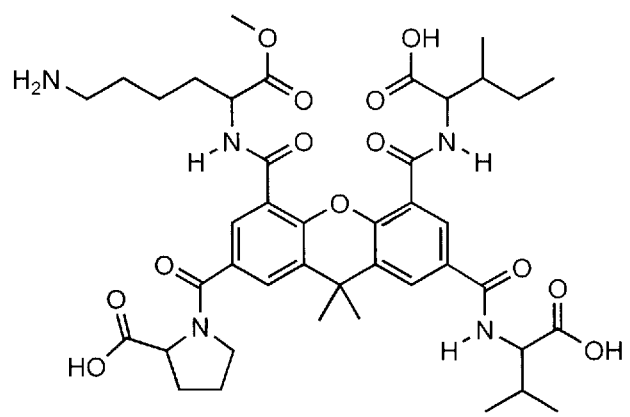

The screening results obtained from these sub-libraries (FIG. 19, Chart D) indicate that only sub-libraries 3A and 3B, in which the combination Lys/Val or Lys/Ile was used as the first set of tool molecules, contained trypsin inhibitor(s). Thus, sub-libraries 3A and 3B each contain a trypsin inhibitor(s) in which a Lys tool molecule is accompanied by Val or Ile at the four and five positions of the xanthene skeleton. In contrast, sub-library 3C, which contained only compounds in which Lys was accompanied by Pro at the four and five positions of the xanthene skeleton, showed no inhibitory activity. The sub-libraries 3D, 3E and 3F, which contained compounds having the Lys tool molecule at the two or seven position of the xanthene skeleton, showed no trypsin inhibitory activity. In view of the foregoing, the structures of potential trypsin inhibitors was limited to the compounds (Formulas V and VI) shown in FIG. 21. These two compounds feature the Lys and the Ile tool molecules in the four and five position but differ in the arrangement of the Pro and Val tool molecules at xanthene position two and seven.

Formulas V and VI were synthesized and fully characterized. The syntheses followed the procedure outlined in FIG. 20. First, compound 3 was reacted with Lys and Ile (Set 1). After isolation of compound ($A_1$=Lys, $A_2$=Ile) by chromatography, subsequent debenzylation and reaction of the resulting diacid with Pro and Val (Set 2) gave four compounds from which $A_1$=Lys, $A_2$=Ile, $B_1$=Pro, $B_2$=Val and $A_1$=Lys, $A_2$=Ile, $B_1$=Val, $B_2$=Pro were obtained by chromatography. Deprotection with Reagent K and purification by reverse phase HPLC gave Formulas V and VI as white powders. All analytical data were in agreement with the proposed structures. Initial experiments indicated that Formula V is a specific trypsin inhibitor because it does not interfere with other proteases, such as thrombin. Despite their structural similarities, Formula V was significantly more active than its structural isomer Formula VI. Preliminary investigations showed that the $K_i$ of Formula V was in the 10 $\mu$M range ($K_i$ approximately $9 \times 10^{-6}$M).

Methods for determining the $K_i$ of an enzyme inhibitor would be known to those of ordinary skill in the art. (See also "Enzyme Kinetics & Behavior, Analysis of Rapid Equilibrium, and Steady State Enzyme Systems", ed. Segel, John Wiley & Sons, Inc., N.Y., N.Y. (1993), the contents of which are incorporated herein by reference.) A summary of the procedure used to obtain the $K_i$ value for compound of Formula V.

A constant amount of trypsin ($7.4 \times 10^{-8}$M) was assayed in the presence of an increasing amount of substrate (BAPA, $2 \times 10^{-4}$M to $7 \times 10^{-3}$M to obtain a typical Michaelis-Menton graph in accordance with standard practice. Next, assays at these enzyme and substrate concentrations were repeated in the presence of five different inhibitor concentrations ranging from $1 \times 10^{-6}$M to $1 \times 10^{-4}$M. Data analysis (e.g., of graphs obtained by plotting 1/velocity vs. 1/(substrate concentration for each concentration of inhibitor) indicated that the compound of Formula V is a competitive inhibitor of trypsin.

The compounds of Formulas V and VI represent the first non-linear peptide inhibitors for an enzyme derived from a library of small organic molecules. By applying an iterative screening procedure, the compound of Formula V with a desired trypsin inhibitory potency was isolated from a vast library in a few weeks. These results evidence the utility of the processes for creating molecular diversity and iterative screening disclosed herein for identifying clinically and industrially relevant lead compounds.

Example 12

A Trypsin Inhibitor Solution for Cell Culture

This protocol is adapted from the protocol entitled, "Technical Information—Trypsin: Using Trypsin to Remove Adherent Cells from a Culture Surface", Sigma Chemical Co. catalog (1993), St. Louis, Mo., in the section on Tissue Culture Media and Reagents.

Adherent cells are cultured according to standard procedures known to one of ordinary skill in the art. The adherent cells are removed from the culture substrate by treatment with trypsin or trypsin-EDTA according to standard procedures. Following trypsinization, the cell suspension is diluted with a trypsin inhibitor solution (described below) to inhibit trypsin activity and avoid prolonged exposure of the cells to trypsin, thereby preventing trypsin-mediated cell damage.

The trypsin inhibitor solution is prepared by dissolving a trypsin inhibitor of the invention (e.g., the compounds of Formulas V and/or VI, see FIG. 21) in cell culture medium (preferably serum-free medium) at a concentration of about 1 mg/ml. Optimization of the concentration needed to inhibit trypsin activity is determined according to standard procedures known to one of ordinary skill in the art with no more than routine experimentation. The inhibitor solution is sterile filtered through a 0.2 um cellulose acetate membrane before use.

Following trypsinization, the cells are resuspended in 1 ml of the trypsin inhibitor solution per ml of trypsin. The cells are centrifuged at 1000 rpm for 5 minutes and as much of the trypsin inhibitor solution is removed as is possible. The pellet containing the cells is resuspended in cell culture medium (e.g., serum-free medium) and the cells are cultured according to standard practice.

Example 13

Identification of Other Serine Proteases

The above-described iterative screening procedure (Examples 8 and 11) is adapted to identify other serine protease inhibitors present in the molecular library by substituting the specific enzyme assay for the serine protease for which an inhibitor is being sought for the trypsin assay. Enzyme assays for thrombin (this can also be assayed by adapting the trypsin assay of Example 11 to substitute thrombin for trypsin and to substitute N-benzoyl-phenylalanine-valine-arginine-p-nitroanilide for the substrate described in the trypsin assay), recombinant HIV protease, elastase, cathepsin G, hemolytic activity, C1, Factor D, Factor $X_a$, plasma Kallikrein, plasmin, and tissue plasminogen activator (t-PA) are disclosed above ("Enzyme Assays").

For example, the library of Example 11 is screened to identify a non-trypsin serine protease inhibitor by observing the inhibitory effect of a series of sub-libraries on the enzymatic activity of the serine protease for which the inhibitor is being sought. In this manner, additional serine protease inhibitors having specific inhibitory activity for one or more of the above-identified proteases are identified.

Each reference identified above is incorporated herein in its entirety by reference. It should be understood that the preceding is merely a detailed description of certain preferred embodiments. It therefore should be apparent to those skilled in the art that various modifications and equivalents can be made without departing from the spirit or scope of the invention.

What is claimed is:

1. A method for forming a combinatorial library, the method comprising:
    (a) admixing a plurality of xanthene molecules with a mixture of amino acids to form a reaction mixture, wherein each of said xanthene molecules has from two to four reactive centers attached thereto, each of said reactive centers is independently selected from the group consisting of an acid halide, epoxide, aldehyde, carboxylic acid, and carboxylic ester, and each of said amino acids has an amine group that is capable of reacting with said reactive centers;
    (b) reacting the reactive centers of the xanthene molecules with the amine groups of the amino acids to form a mixture of library molecules.

2. The method of claim 1, wherein the amino acids further include a secondary functional group, the method further comprising the step of protecting the secondary functional group with a protecting agent prior to admixing the plurality of xanthene molecules with the mixture of amino acids.

3. The method of claim 1, further comprising the step of:
    (c) separating the unreacted xanthene molecules and the unreacted amino acids from the library molecules.

4. The method of claim 3, wherein the xanthene molecules and the amino acids are water-soluble and the library molecules are fat-soluble and wherein separating the xanthene molecules and the amino acids from the library molecules comprises extracting the unreacted xanthene molecules and the unreacted amino acids from the fat-soluble library molecules.

5. The method of claims 3, wherein the library molecules are biologically-inactive, further comprising the step of:

(d) converting the library molecules into a biologically-active state.

6. The method of claim 5, wherein the library molecules include a protecting group and wherein converting the library molecules into a biologically-active state comprises removing the protecting group from the library molecules.

7. The method of claim 1, wherein the xanthene molecule is 9,9-dimethyl xanthene 2,4,5,7-tetraacid chloride.

8. A kit for forming a combinatorial library, comprising:

a plurality of xanthene molecules, each xanthene molecule having from two to four reactive centers attached thereto, and each of said reactive centers being independently selected from the group consisting of an acid halide, epoxide, aldehyde carboxylic acid, and carboxylic ester;

a mixture of amino acids, each of said amino acids having an amine group, and instructions for reacting the reactive centers of the xanthene molecules with the amine groups of the amino acids to form a combinatorial library.

9. A combinatorial library produced by the process of claim 1.

10. A method for forming a combinatorial library, the method comprising:

(a) admixing a plurality of xanthene molecules with a mixture of amines, said amines selected from the group consisting of a primary amine and a secondary amine, to form a reaction mixture, wherein each of said xanthene molecules has from two to four reactive centers attached thereto, each of said reactive centers is independently selected from the group consisting of an acid halide, epoxide, aldehyde, carboxylic acid, and carboxylic ester, and each of said amines has an amine group that is capable of reacting with said reactive centers; and (b) reacting the reactive centers of the xanthene molecules with the amino groups of the amines to form a mixture of library molecules.

11. The method of claim 10, wherein the amines further include a secondary functional group, the method further comprising the step of protecting the secondary functional group with a protecting agent prior to admixing the plurality of xanthene molecules with the mixture of amines.

12. The method of claim 10, further comprising the step of:

(c) separating the unreacted xanthene molecules and the unreacted amines from the library molecules.

13. The method of claim 12, wherein the xanthene molecules and the amines are water-soluble and the library molecules are fat-soluble and wherein separating the xanthene molecules and the amines from the library molecules comprises extracting the unreacted xanthene molecules and the unreacted amines from the fat-soluble library molecules.

14. The method of claim 12, wherein the library molecules are biologically-inactive, further comprising the step of:

(d) converting the library molecules into a biologically-active state.

15. The method of claim 14, wherein the library molecules include a protecting group and wherein converting the library molecules into a biologically-active state comprises removing the protecting group from the library molecules.

16. The method of claim 10, wherein the xanthene molecule is 9,9-dimethyl xanthene 2,4,5,7-tetraacid chloride.

17. A kit for forming a combinatorial library, comprising:

a plurality of xanthene molecules, each xanthene molecule having from two to four reactive centers attached thereto, and each of said reactive centers being independently selected from the group consisting of an acid halide, epoxide, aldehyde, carboxylic acid, and carboxylic ester;

a mixture of amines, said amines selected from the group consisting of a primary amine and a secondary amine, each of said aminos having an amine group that is capable of reacting with said reactive centers; and instructions for reacting the reactive centers of the xanthene molecules with the amine groups of the amines to form a combinatorial library.

18. A combinatorial library produced by the process of claim 10.

* * * * *